United States Patent [19]

Ikawa et al.

[11] Patent Number: 5,616,711
[45] Date of Patent: Apr. 1, 1997

[54] METHODS OF PRODUCING AMINOBUTENE DERIVATIVES

[75] Inventors: Hiroshi Ikawa; Hajime Matsumoto, both of Tokyo; Masakatsu Matsumoto, Sagamihara; Yasuo Sekine, Tokyo; Masato Nishimura, Tokyo; Akihiko Hosoda, Tokyo, all of Japan

[73] Assignee: Fujirebio Inc., Tokyo, Japan

[21] Appl. No.: 102,819

[22] Filed: Aug. 6, 1993

[30]     Foreign Application Priority Data

Aug. 7, 1992  [JP]  Japan ........................... 4-231498
Aug. 7, 1992  [JP]  Japan ........................... 4-231499
Sep. 30, 1992 [JP]  Japan ........................... 4-283575
Nov. 6, 1992  [JP]  Japan ........................... 4-321365

[51] Int. Cl.$^6$ .............. C07C 233/00; C07D 211/68; C07D 211/36; C07D 217/22
[52] U.S. Cl. .......... 546/141; 546/146; 546/153; 546/169; 546/193; 546/194; 546/195; 546/197; 546/201; 546/203; 546/205; 546/207; 546/212; 546/214; 546/220; 546/233; 546/242; 546/244; 546/246; 549/76; 549/77; 549/419; 549/450; 549/452; 560/29; 560/31; 560/160; 564/123; 564/161; 564/192; 564/209; 564/215; 564/224
[58] Field of Search .................. 564/224, 192, 564/123, 161, 209, 215; 546/193, 220, 242, 233, 141, 146, 153, 194, 195, 197, 201, 203, 205, 207, 212, 214, 244, 246, 169; 560/160, 29, 31; 549/419, 452, 76, 77, 450

[56]                References Cited

U.S. PATENT DOCUMENTS 4,353,828  10/1982  Bey et al. ..................... 564/215

FOREIGN PATENT DOCUMENTS 0177016  4/1986  European Pat. Off. .
0282077  9/1988  European Pat. Off. .

OTHER PUBLICATIONS

Journal of the Chemical Society, Perkin Transactions 1, vol. 1, No. 4, 1991, pp. 705–713, Jeremy Cooper, et al., "An Approach To Chiral Trisubstituted Pyrrolidines By Enolate Claisen Rearrangement of Azalactones Derived From Alpha–Amino Acids".

*Primary Examiner*—C. Warren Ivy
*Assistant Examiner*—Raymond Covington
*Attorney, Agent, or Firm*—Oblon, Spivak, McClelland, Maier & Neustadt, P.C.

[57]                ABSTRACT

A method of producing an aminobutene derivative of formula (I) by allowing a butenol derivative of formula (II) to react with an amide derivative of formula (III) is disclosed. The aminobutene derivative of formula (I) can be deprotected to produce an aminobutene derivative of formula (I-1) or an aminobutene derivative of formula (I-2):

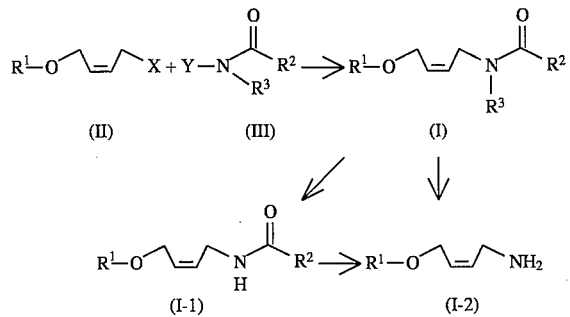

The aminobutene derivative of formula (I-A) can also be deprotected to produce the aminobutene derivative of formula (I-B). Any or all of the above aminobutene derivatives are useful as intermediates for producing anti-ulcer drugs, and anti-ulcer drugs having an inhibitory effect on gastric acid secretion based on the antagonism against histamine $H_2$ receptor.

24 Claims, No Drawings

METHODS OF PRODUCING AMINOBUTENE DERIVATIVES

BACKGROUND OF THE INVENTION

1. Field of the Invention

The present invention relates to a method of producing aminobutene derivatives which are useful as intermediates for producing anti-ulcer drugs, and which are also useful as anti-ulcerdrugs having an inhibitory effect on gastric acid secretion based on the antagonism against histamine $H_2$ receptor.

2. Discussion of Background

The following aminobutene derivatives of formula (I-1) and (I-2) are known as intermediates for producing anti-ulcer drugs (refer to Japanese Laid-Open Patent Application 63-225371):

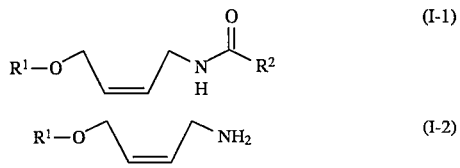

wherein $R^1$ represents hydrogen; a protective group for hydroxyl group, an aromatic hydrocarbon group which may have a substituent, or a heterocyclic group which may have a substituent; and $R^2$ represents hydrogen, an alkoxyl group, an alkyl group which may have a substituent, an aromatic hydrocarbon group which may have a substituent, or a heterocyclic group which may have a substituent.

Furthermore, the following aminobutene derivative of formula (I-3), which may be referred to as pyridyloxy derivative, is known as an intermediate for producing a remedy for peptic ulcer, and also as a remedy for peptic ulcer as having an inhibitory effect on gastric acid secretion based on the antagonism against histamine $H_2$ receptor (refer to Japanese Laid-Open Patent Application 63-225371):

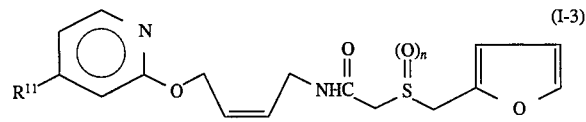

wherein $R^{11}$ represents hydroxymethyl group, tetrahydropyranyl-2-oxymethyl group, methoxymethoxymethyl group, formyl group, dimethoxymethyl group, diethoxymethyl group, 1,3-dioxolan-2-yl group, piperidinomethyl group, or dimethylamino methyl group; and n is an integer of 0, 1 or 2.

The aminobutene derivative of formula (I-2) is conventionally produced by the Gabriel reaction in which a phthalimide compound is allowed to react with a halogenated compound to introduce an amino group into the halogenated compound.

Alternatively, the above aminobutene derivative of formula (I-2) is conventionally produced by replacing the phthalimide compound employed in the above reaction with an azide compound (refer to Japanese Laid-Open Patent Application 2-121969), or by a method using a dioxathiepin derivative (refer to Japanese Laid-Open Patent Application 3-209349).

The above-mentioned methods, however, have the shortcomings that many steps are necessary for producing the aminobutene derivative, expensive reagents are required, the yield of the aminobutene derivative is low because of the formation of excessive by-products, and the isolation of the desired aminobutene derivative from the by-products is extremely difficult, so that the above methods are not suitable for industrial methods for producing the aminobutene derivative of formula (I-2).

As a matter of course, the production of the aminobutene derivative of formula (I-1) is also conventionally difficult because the aminobutene derivative of formula (I-1) is conventionally produced by the acylation of the aminobutene derivative of (I-2).

Furthermore, the previously mentioned aminobutene derivative of formula (I-3), which may be referred to as pyridyloxy derivative, can be produced by condensing an amine compound and a carboxylic acid compound (refer to Japanese Laid-Open Patent Application 63-225371 and Japanese Laid-Open Patent Application 1-193247).

However, a conventional method for producing the amine compound to be used as a starting material for the production of the pyridyloxy derivative, has many serious problems, such as too many production steps being included, complicated treatments using expensive reagents being necessary, and the yield of the amine compound being extremely low because of the formation of excessive by-products.

On the other hand, the carboxylic acid compound which is the other starting material for the production of the aminobutene derivative of formula (I-3) is used in the form of an active ester derivative, and when synthesizing the active ester derivative, expensive reagents must be used. Furthermore, in the condensation reaction between the amine compound and the carboxylic acid compound, by-products are formed in a large amount and complicated steps are required for removing the by-products for the isolation of the desired aminobutene derivative of formula (I-3). Thus, the above method is not suitable for industrial production of the aminobutene derivative of formula (I-3).

Aminobutenol of formula,

which can be used as an intermediate for producing the above-mentioned aminobutene derivatives, is conventionally produced by any of the following methods:

(1) A method of subjecting aminobutenol to catalytic reduction [Andree Marszak-Flenry et al., Bull. Soc. Chim. France, 6, 1270 (1963)], (2) A method of subjecting dihydrooxadine to reducing ring opening [O. Wichterle et. al., Collect. Czech. Chem. Commun, 15, 309 (1905)], and (3) A method of liberating aminobutenol from an aminobutenol protected by phthalimide (Japanese Laid-Open Patent Application 3-209349].

The above method (1) has the shortcomings that it is difficult to terminate the reaction of catalytic reduction so as to selectively obtain aminobutenol, and it is also difficult to control the geometric isomerism of the double bond of the product. The above method (2) has the shortcoming that it is difficult to obtain dihydroxadine serving as a starting material for the synthesis of aminobutenol by an industrial production method. The above method (3) has the shortcomings that the procedure of the method itself is complicated, aminobutenol cannot be obtained selectively, and the isolation of aminobutenol is extremely difficult.

SUMMARY OF THE INVENTION

It is therefore a first object of the present invention to provide a method of producing an aminobutene derivative of formula (I), which is free from the above-mentioned shortcomings of the conventional methods:

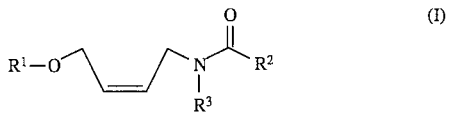

wherein $R^1$ represents hydrogen; a protective group for hydroxyl group, an aromatic hydrocarbon group which may have a substituent, or a heterocyclic group which may have a substituent; $R^2$ represents hydrogen, an alkoxyl group, an alkyl group which may have a substituent, an aromatic hydrocarbon group which may have a substituent, or a heterocyclic group which I may have a substituent; and $R^3$ represents hydrogen, an acyl group which may have a substituent, an alkoxy-carbonyl group, sulfonyl group, or a substituted alkyl group.

A second object of the present invention is to provide a method of producing an aminobutene derivative of formula (I-1):

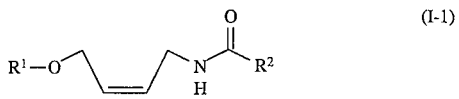

wherein $R^1$ and $R^2$ are respectively the same as those defined in formula (I).

A third object of the present invention is to provide a method of producing an aminobutene derivative of formula (I-2):

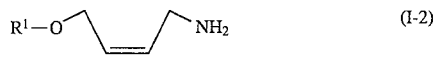

wherein $R^1$ is the same as defined in formula (I).

A fourth object of the present invention is to provide a method of producing an aminobutene derivative of formula (I-3), which may be referred to as a pyridyloxy derivative:

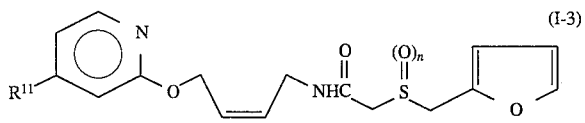

wherein $R^{11}$ represents hydroxymethyl group, tetrahydropyranyl-2-oxymethyl group, methoxymethoxymethyl group, formyl group, dimethoxymethyl group, diethoxymethyl group, 1,3-dioxolan-2-yl group, piperidinomethyl group, or dimethylamino methyl group.

A fifth object of the present invention is to provide a method of producing an aminobutene derivative of formula (I-3a):

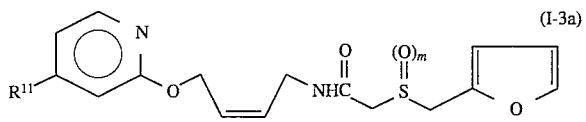

wherein $R^{11}$ is the same as in the formula (I-3), and m is n+1, in which n is 0 or 1.

Any or all of the above aminobutene derivatives are useful as intermediates for producing anti-ulcer drugs, or which are also useful as anti-ulcer drugs having an inhibitory effect on gastric acid secretion based on the antagonism against histamine $H_2$ receptor.

The first object of the present invention of producing the aminobutene derivative of formula (I) can be attained by allowing a butene derivative of formula (II) to react with an amide derivative of formula (III) in accordance with the following reaction scheme (A):

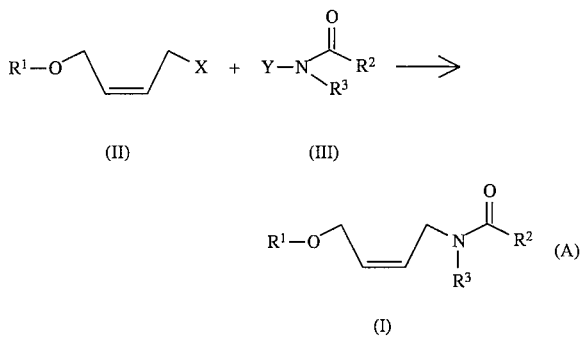

wherein $R^1$, $R^2$ $R^3$ are respectively the same as previously defined in formula (I); X represents hydroxyl group, a halogen atom, a sulfonyloxy group, an acyloxy group, an alkoxy-carbonyloxy group, or a group which can form a cyclic sulfurous ester, sulfuric ester or carbonic acid ester in combination with $R^1$; and Y represents an alkali metal, an alkaline earth metal, or hydrogen.

The second object of the present invention of producing the aminobutene derivative of formula (I-1) can be achieved by using an amide derivative of formula (III) in which $R^3$ is hydrogen in the above-mentioned reaction scheme (A), or by subjecting the aminobutene derivative of formula (Ia) to deprotection in accordance with the following reaction scheme (B):

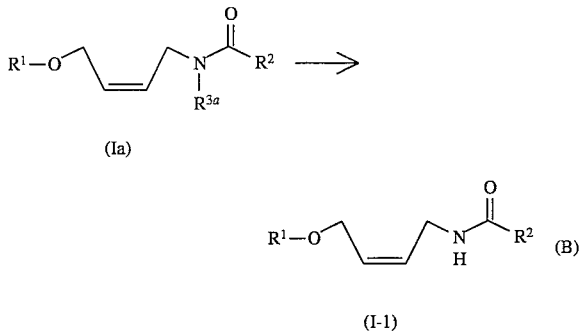

wherein $R^1$ represents hydrogen; a protective group for hydroxyl group, an aromatic hydrocarbon group which may have a substituent, or a heterocyclic group which may have a substituent; $R^2$ represents hydrogen, an alkoxyl group, an alkyl group which may have a substituent, an aromatic hydrocarbon group which may have a substituent, or a heterocyclic group which may have a substituent; and $R^{3a}$ represents an acyl group which may have a substituent, an alkoxy-carbonyl group, sulfonyl group, or a substituted alkyl group.

The third object of the present invention of producing the aminobutene derivative of formula (I-2) can be achieved by subjecting the aminobutene derivative of formula (I) to deprotection in accordance with the following reaction scheme (C) or by subjecting the aminobutene derivative of formula (I-1) to deprotection in accordance with the following reaction scheme (D):

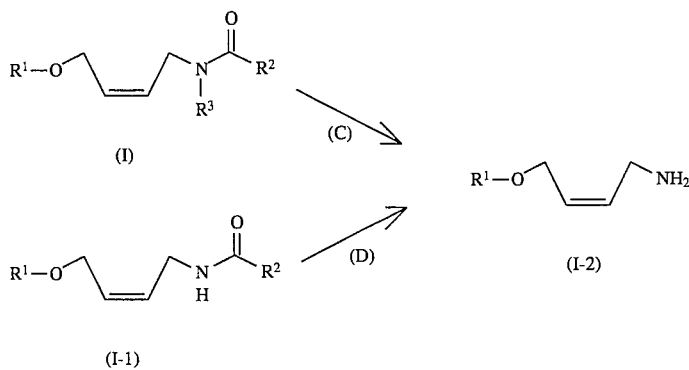

The fourth object of the present invention of producing the aminobutene derivative of formula (I-3) can be achieved by the condensation reaction in accordance with the previously mentioned reaction scheme (A):

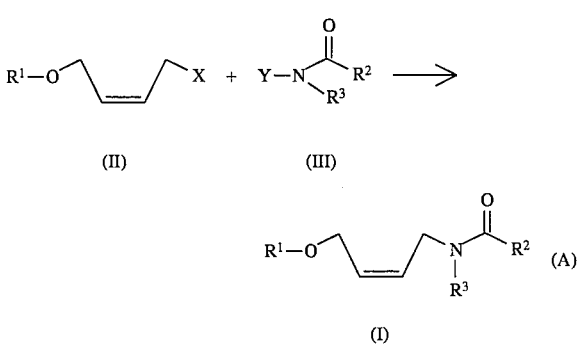

More specifically, as the butene derivative of formula (II), there is employed a butene derivative of formula (II) in which $R^1$ is

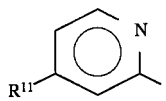

wherein $R^{11}$ represents hydroxymethyl group, tetrahydropyranyl-2-oxymethyl group, methoxymethoxymethyl group, formyl group, dimethoxymethyl group, diethoxymethyl group, 1,3-dioxolan-2-yl group, piperidinomethyl group, or dimethylamino methyl group; and X represents a halogen atom, hydroxyl group, methane sulfonyloxy group, p-toluene sulfonyloxy group, or benzene sulfonyloxy group, and as the amine derivative of formula (III), there is employed an amide derivative of formula (III) in which $R^2$ represents

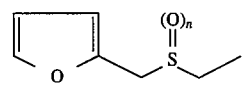

in which n is an integer of 0, 1 or 2; and $R^3$ represents hydrogen, whereby the aminobutene derivative of formula (I-3) is produced:

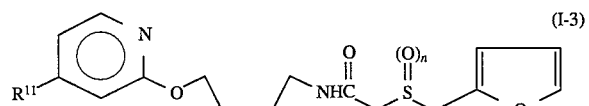

The above aminobutene derivative of formula (I-3) may also be referred to as pyridyloxy derivative.

The fifth object of the present invention of producing the aminobutene derivative of formula (I-3a) can be achieved by oxidizing the above-mentioned aminobutene derivative of formula (I-3) in the following reaction scheme (E):

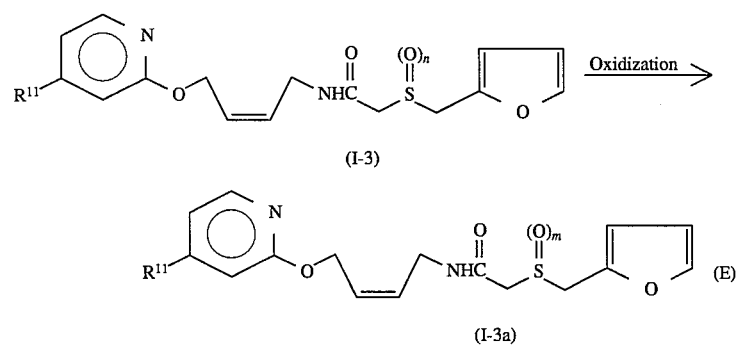

wherein $R^{11}$ is the same as in the formula (I-3), and m is n+1, in which n is 0 or 1.

DETAILED DESCRIPTION OF THE PREFERRED EMBODIMENTS

According to the present invention, there is provided a method of producing an aminobutene derivative of formula (I) by allowing a butene derivative of formula (II) to react with an amide derivative of formula (III) in accordance with the following reaction scheme (A):

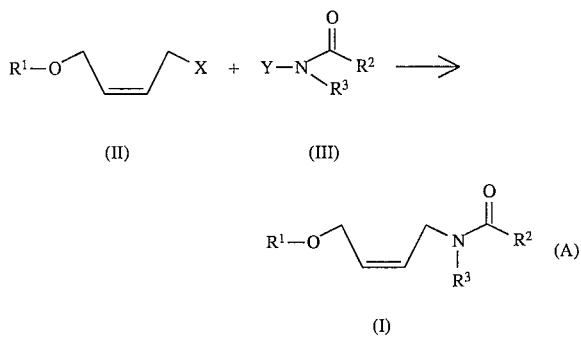

wherein $R^1$ represents hydrogen; a protective group for hydroxyl group, an aromatic hydrocarbon group which may have a substituent, or a heterocyclic group which may have a substituent; X represents hydroxyl group, a halogen atom, a sulfonyloxy group, an acyloxy group, an alkoxy-carbonyloxy group, or a group which can form a cyclic sulfurous ester, sulfuric ester or carbonic acid ester in combination with $R^1$; Y represents an alkali metal, an alkaline earth metal, or hydrogen; $R^2$ represents hydrogen, an alkoxyl group, an alkyl group which may have a substituent, an aromatic hydrocarbon group which may have a substituent, or a heterocyclic group which may have a substituent; and $R^3$ represents hydrogen, an acyl group which may have a substituent, an alkoxy-carbonyl group, sulfonyl group, or a substituted alkyl group.

In the above butene derivative of formula (II), examples of the protective group for hydroxyl group represented by $R^1$ are tetrahydropyranyl group, methoxymethyl group, benzyloxymethyl group, ethoxyethyl group, 2-methoxyethyl group, t-butyl group, benzyl group, 4-methoxybenzyl group, diphenylmethyl group, triphenylmethyl group, trimethylsilyl group, triethylsilyl group, t-butyl dimethylsilyl group, formyl group, acetyl group, n-propionyl group, iso-propionyl group, n-butyryl group, iso-butyryl group, valeryl group, iso-valeryl group, pivaloyl group, benzoyl group, naphthoyl group, methoxycarbonyl group, ethoxycarbonyl group, iso-butoxycarbonyl group, allyloxycarbonyl group, benzyloxycarbonyl group, 9-fluorenylmethoxycarbonyl group, and phenyloxycarbonyl group.

Examples of the aromatic hydrocarbon group represented by $R^1$ in the butene derivative of formula (II) are phenyl group, naphthyl group, anthranyl group, 3-(tetrahydropyranyl-2-oxymethyl)phenyl group, 3-(methoxymethoxymethyl)phenyl group, 3-formylphenyl group, 3-(diethoxymethyl)phenyl group, 3-(1,3-dioxolan-2-yl)-phenyl group, 3-(piperidino-methyl)phenyl group, 3-(dimethylaminomethyl)phenyl group, 4-(tetrahydropyranyl-2-oxymethyl)phenyl group, 4-(methoxymethoxymethyl)phenyl group, 4-formylphenyl group, 4-(diethoxymethyl)phenyl group, 4-(1,3-dioxolan-2-yl)phenyl group, 4-(piperidinomethyl)phenyl group, 4-(dimethylaminomethyl)phenyl group, 2-(tetrahydropyranyl-2-oxymethyl)phenyl group, 2-(methoxymethoxymethyl)phenyl group, 2-formylphenyl group, 2-(diethoxymethyl)phenyl group, 2-(1,3-dioxolan-2-yl)phenyl group, 2-(piperidinomethyl)phenyl group, and 2-(dimethyl aminomethyl)phenyl group.

Examples of the heterocyclic group represented by $R^1$ in the butene derivative of formula (II) are pyridyl group, quinolyl group, iso-quinolyl group, thienyl group, furyl group, 3-(tetrahydropyranyl-2-oxymethyl)-2-pyridyl group, 3-(methoxymethoxymethyl)-2-pyridyl group, 3-formyl-2-pyridyl group, 3-(diethoxymethyl)-2-pyridyl group, 3-(1,3-dioxolan-2-yl)-2-pyridyl group, 3-(piperidino-methyl)-2-pyridyl group, 3-(dimethylaminomethyl)-2-pyridyl group, 4-(tetrahydropyranyl-2-oxymethyl)-2-pyridyl group, 4-(methoxymethoxymethyl)-2-pyridyl group, 4-formyl-2-pyridyl group, 4-(diethoxymethyl)-2-pyridyl group, 4-(1,3-dioxolan-2-yl)-2-pyridyl group, 4-(piperidinomethyl)-2-pyridyl group, 4-(dimethylaminomethyl)-2-pyridyl group, 5-(tetrahydropyranyl-2-oxymethyl)-2-pyridyl group, 5-(methoxymethoxymethyl)-2-pyridyl group, 5-formyl-2-pyridyl group, 5-(diethoxymethyl)-2-pyridyl group, 5-(1,3-dioxolan-2-yl)-2-pyridyl group, 5-(piperidinomethyl)-2-pyridyl group, and 5-(dimethylaminomethyl)-2-pyridyl group.

Examples of the halogen atom represented by X in the butene derivative of formula (II) are chlorine, bromine and iodine.

Examples of the sulfonyloxy group represented by X in the butene derivative of formula (II) are methanesulfonyloxy group, trifluoromethanesulfonyloxy group, benzenesulfonyloxy group, p-toluenesulfonyloxy group, and imidazosulfonyloxy group.

Examples of the acyloxy group represented by X in the butene derivative of formula (II) are formyloxy group, acetyloxy group, n-propionyloxy group, isopropionyloxy group, n-butyryloxy group, iso-butyryloxy group, valeryloxy group, iso-valeryloxy group, pivaloyloxy group, benzoyloxy group, and naphthoyloxy group.

Examples of the alkoxy-carbonyloxy group represented by X in the butene derivative of formula (II) are methoxycarbonyloxy group, ethoxy-carbonyloxy group, isobutoxycarbonyloxy group, allyloxy-carbonyloxy group, benzyloxycarbonyloxy group, 9-fluorenylmethoxycarbonyloxy group, and phenyoxy-carbonyloxy group.

Specific examples of the butene derivative of formula (II) are 4,7-dihfydro-1,3,2-dioxathiepin-2-oxide, 4,7-dihydro-1,3,2-dixathiepin-2,2-dioxide, and 4,7-dihydro-1,3,2-dioxepin-2-oxide.

Examples of the alkali metal represented by Y in the amide derivative of formula (III) are lithium, sodium, potassium, rubidium and cesium. Examples of the alkali earth metal represented by Y in the amide derivative of formula (III) are magnesium and calcium.

Examples of the alkoxyl group represented by $R^2$ in the amide derivative of formula (III) are methoxy group, ethoxy group, propoxy group, iso-butoxy group, t-butoxy group, and benzyloxy group.

Examples of the alkyl group represented by $R^2$ in the amide derivative of formula (III) are methyl group, ethyl group, propyl group, butyl group, chloromethyl group, dichloromethyl group, trichloromethyl group, trifluoromethyl group, benzyl group, furfurylthiomethyl group, furfurylsulfinylmethyl group, and furfurylsulfonylmethyl group.

Examples of the aromatic hydrocarbon group represented by $R^2$ in the amide derivative of formula (III) are phenyl group, naphthyl group, and anthryl group. These aromatic hydrocarbon groups may have a substituent such as an alkyl group, an alkoxyl group, a halogen atom, nitro group, and an amino group.

Examples of the heterocyclic group represented by $R^2$ in the amide derivative of formula (III) are pyridyl group, quinolyl group, iso-quinolyl group, thienyl group, and furyl group. These heterocyclic group may have a substituent such as an alkyl group, an alkoxyl group, a halogen atom, nitro group, and an amino group.

Examples of the acyl group represented by $R^3$ in the amide derivative of formula (III) are formyl group, acetyl group, propionyl group, butyryl group, valeryl group, chloro-acetyl group, dichloroacetyl group, trichloroacetyl group, trifluoroacetyl group, phenylacetyl group, benzoyl group, naphthoyl group, furoyl group, thenoyl group, nicotinoyl group, and isonicotinoyl group.

Examples of the alkoxy-carbonyl group represented by $R^3$ in the amide derivative of formula (III) are methoxycarbonyl group, ethoxycarbonyl group, iso-butoxycarbonyl group, allyloxycarbonyl group, benzyloxycarbonyl group, 9-fluorenylmethoxycarbonyl group, and phenyloxycarbonyl group.

Examples of the sulfonyl group represented by $R^3$ in the amide derivative of formula (III) are methanesulfonyl group, trifluoromethanesulfonyl group, benzenesulfonyl group, p-toluenesulfonyl group, and imidazosulfonyl group.

Examples of the substituted alkyl group represented by $R^3$ in the amide derivative of formula (III) are benzyl group, 4-methoxybenzyl group, and 2,4-dimethoxybenzyl group.

In producing the aminobutene derivative of formula (I) by allowing the butene derivative of formula (II) to react with the amide derivative of formula (III) in accordance with the following reaction scheme (A),

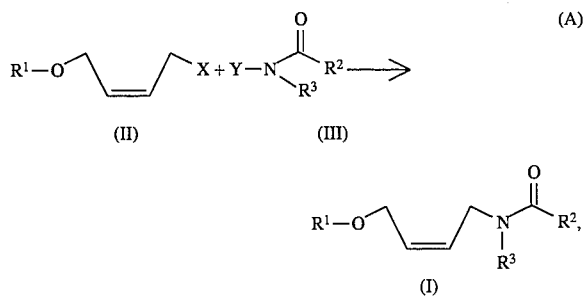

the butene derivative of formula (II) can be easily produced from 2-butene-1,4-diol which is easily available.

In the butene derivative of formula (II), X represents any of the previously mentioned groups, which can undergo a condensation reaction with the amide derivative of formula (III).

The reaction between the butene derivative of formula (II) and the amide derivative of formula (III) can be caused to proceed by mixing the two to obtain the aminobutene derivative of formula (I). In order to cause the reaction to proceed smoothly, it is preferable to employ a base.

Examples of the base for use in the above reaction are alkali metal hydroxides such as sodium hydroxide and potassium hydroxide; alkoxides such as potassium t-butoxide and sodium methoxide; alkali metal hydrides such as sodium hydride and lithium hydride; alkali metals such as sodium and potassium; and organic amines such as triethylamine and pyridine. Such a base can be generally employed in an amount of 0.1 to 2.0 equivalents to the butene derivative of the formula (II).

It is preferable that the above reaction be carried out in an inert solvent. Examples of the inert solvent are aromatic hydrocarbons such as benzene, toluene and xylene; ethers such as THF, dioxane and DME; halogenated hydrocarbons such as dichloromethane, chloroform, and dichloroethane; ethyl acetate; methyl ethyl ketone; acetone; acetonitrile; DMF; dimethylacetamide; and DMSO.

The reaction proceeds at −100° C. to 200° C., but it is preferable that the reaction be carried out at 0° C. to 100° C. to cause the reaction to proceed efficiently.

Furthermore, in order to cause the reaction to proceed more efficiently, catalysts such as tetrabutylammonium hydrogen sulfate, tetrabutylammonium chloride, triethylbenzylammonium chloride, crown ether, and hexadecyltributyl phosphonium bromide can be employed. The above catalysts can be employed in an amount of 0,001 to 1 equivalent to the butene derivative of formula (II).

An aminobutene derivative of the following formula (I-1):

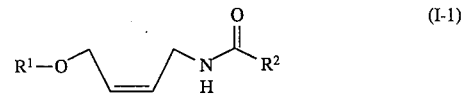

wherein $R^1$ and $R^2$ are respectively the same as defined in formula (I), can be produced in the same manner as mentioned above, specifically by allowing the butene derivative of formula (II) to react with an amide derivative of formula (III-1) in the following reaction scheme:

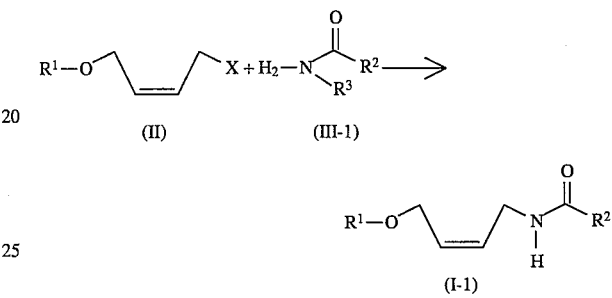

wherein $R^2$ is the same as mentioned above in formula (III).

Furthermore, according to the present invention, an aminobutene derivative of formula (I-3), which may be referred to as pyridyloxy derivative, can be prepared by allowing a pyridyloxybutenyl derivative of formula (II-1) to react with an acetamide derivative of formula (III-2) as follows:

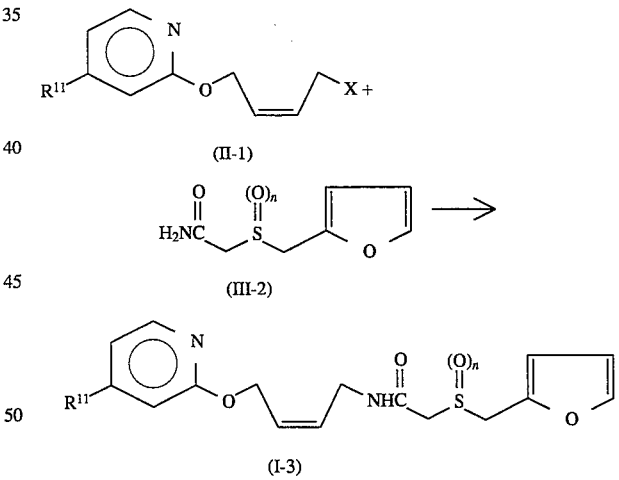

wherein $R^{11}$ represents hydroxymethyl group, tetrahydropyranyl-2-oxymethyl group, methoxymethoxymethyl group, formyl group, dimethoxymethyl group, diethoxymethyl group, 1,3-dioxolan-2-yl group, piperidinomethyl group, or dimethylamino methyl group; X represents hydroxyl group, a halogen atom such as chlorine, bromine or iodine, a substituted sulfonyloxy group such as methanesulfonyloxy group, trifluoromethanesulfonyloxy group, benzenesulfonyloxy group, p-toluenesulfonyloxy group, and imidazosulfonyloxy group; and n is an integer of 0, 1 or 2.

The above-mentioned pyridyloxybutenyl derivative of formula (II-1) can be easily obtained, for example, by allowing a 2-chloropyridine derivative having the substituent at a 4-position to react with a 2-butenol derivative.

The above-mentioned acetamide derivative of formula (III-2) can be produced by allowing furfuryl mercaptan to react with 2-chloroacetamide or by allowing p-nitrophenyl 2-furfurylsulfinyl acetate to react with ammonia.

The reaction between the pyridyloxybutenyl derivative of formula (II-1) and the acetamide derivative of formula (III-2) can be caused to proceed by mixing the two to obtain the pyridyloxy derivative of formula (I-3).

In order to cause the reaction to proceed smoothly, it is preferable to employ a base.

Examples of the base for use in the above reaction are alkali metal hydroxides such as sodium hydroxide and potassium hydroxide; alkoxides such as potassium t-butoxide and sodium methoxide; alkali metal hydrides such as sodium hydride and lithium hydride; alkali metals such as sodium and potassium; and organic amines such as triethylamine and pyridine. Such a base can be generally employed in an amount of 0.1 to 2.0 equivalents to the pyridyloxybutenyl derivative of the formula (II-1).

It is preferable that the above reaction be carried out in an inert solvent. Examples of the inert solvent are aromatic hydrocarbons such as benzene, toluene and xylene; ethers such as THF, dioxane and DME; halogenated hydrocarbons such as dichloromethane, chloroform, and dichloroethane; ethyl acetate; methyl ethyl ketone; acetone; acetonitrile; DMF; dimethylacetamide; and DMSO.

The reaction proceeds at −100° C. to 200° C., but it is preferable that the reaction be carried out at 0° C. to 100° C. to cause the reaction to proceed efficiently.

Furthermore, in order to cause the reaction to proceed more efficiently, catalysts such as tetrabutylammonium hydrogen sulfate, tetrabutylammonium chloride, triethylbenzylammonium chloride, crown ether, and hexadecyltributyl phosphonium bromide can be employed. The above catalysts can be employed in an amount of 0.001 to 1 equivalent to the pyridyloxybutenyl derivative represented by the previously mentioned formula (II-1).

According to the present invention, an acetimide compound of formula of formula (I-4) can be produced by allowing the previously mentioned pyridyloxybutenyl derivative of formula (II-1) to react with an imide derivative of formula (III-3) in accordance with the following reaction scheme:

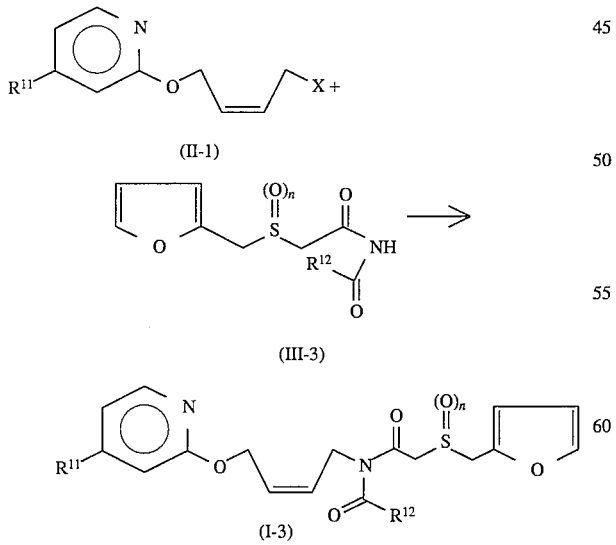

wherein $R^{11}$ and X are respectively the same as mentioned previously; and $R^{12}$ represents hydrogen; an alkyl group having 1 to 6 carbon atoms, such as methyl group, ethyl group, propyl group, butyl group, pentyl group, and hexyl group; an aromatic hydrocarbon group such as phenyl group and naphthyl group, which may have a substituent; an alkoxyl group having 1 to 6 carbon atoms such as methoxy group, ethoxy group, propoxy group, butoxy group, pentyloxy group, and hexyloxy group; or an aryloxy group, such as phenoxy group and naphthyloxy group; and n is an integer of 0, 1 or 2.

The above-mentioned imide derivative of formula (III-3) can be produced by allowing furfuryl mercaptan to react with 2-chloroacetamide to produce an intermediate, followed by the acylation of the intermediate, or by allowing p-nitrophenyl 2-furfurylsulfinyl acetate to react with ammonia to produce an intermediate, followed by the acylation of the intermediate.

The reaction between the pyridyloxybutenyl derivative of formula (II-1) and the imide derivative of formula (III-3) can be caused to proceed by mixing the two to obtain the acetimide derivative of formula (I-4).

In order to cause the reaction to proceed smoothly, it is preferable to employ a base.

Examples of the base for use in the above reaction are alkali metal hydroxides such as sodium hydroxide and potassium hydroxide; alkali carbonates such as potassium carbonate and sodium carbonate; alkoxides such as sodium methoxide, sodium ethoxide and potassium t-butoxide; alkali metal hydrides such as sodium hydride and lithium hydride; alkali metals such as sodium and potassium; and organic amines such as triethylamine and pyridine. Such a base can be generally employed in an amount of 0.1 to 2.0 equivalents to the pyridyloxybutenyl derivative of the formula (II-1).

It is preferable that the above reaction be carried out in an inert solvent. Examples of the inert solvent are aromatic hydrocarbons such as benzene, toluene and xylene; ethers such as THF, dioxane and DME; halogenated hydrocarbons such as dichloromethane, chloroform, and dichloroethane; ethyl acetate; methyl ethyl ketone; acetone; acetonitrile; DMF; dimethylacetamide; and DMSO.

The reaction proceeds at −100° C. to 200° C., but it is preferable that the reaction be carried out at 0° C. to 100° C. to cause the reaction to proceed efficiently.

Furthermore, in order to cause the reaction to proceed more efficiently, catalysts such as tetrabutylammonium hydrogen sulfate, tetrabutylammonium chloride, triethylbenzylammonium chloride, crown ether, and hexadecyltributyl phosphonium bromide can be employed.

The above catalysts can be employed in an amount of 0.001 to 1 equivalent to the pyridyloxybutenyl derivative represented by the previously mentioned formula (II-1).

According to the present invention, the aminobutene derivative of formula (I-2) can be produced by subjecting an aminobutene derivative of formula (Ia) to deprotection in accordance with the following reaction scheme (B) as mentioned previously:

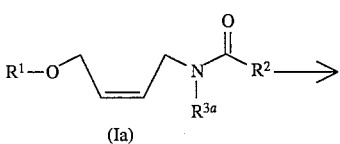

-continued

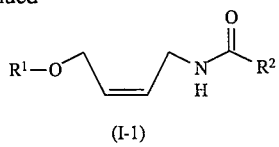

Furthermore, according to the present invention, the aminobutene derivative of formula (I-1) can be produced by subjecting the aminobutene derivative of formula (I) to deprotection in accordance with the following reaction scheme (C) or by subjecting the aminobutene derivative of formula (I-1) to deprotection in accordance with the following reaction scheme (D) as mentioned previously:

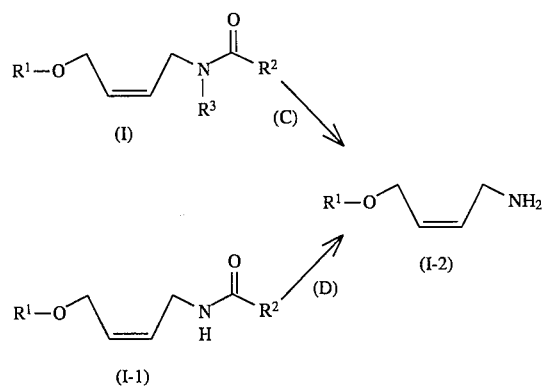

In the above reaction schemes (B), (C) and (D), $R^1$, $R^2$ and $R^3$ are respectively the same as previously defined in the aminobutene derivative of formula (I); and $R^{3a}$ represents the same as represented by $R^3$ except that $R^{3a}$ does not represent hydrogen, namely $R^{3a}$ represents an acyl group which may have a substituent, an alkoxy-carbonyl group, sulfonyl group, or a substituted alkyl group.

Examples of the acyl group represented by $R^{3a}$ in the amide derivative of formula (Ia) are formyl group, acetyl group, propionyl group, butyryl group, valeryl group, chloroacetyl group, dichloroacetyl group, trichloroacetyl group, trifluoroacetyl group, phenylacetyl group, benzoyl group, naphthoyl group, furoyl group, thenoyl group, nicotinoyl group, and isonicotinoyl group.

Examples of the alkoxy-carbonyl group represented by $R^{3a}$ in the amide derivative of formula (Ia) are methoxycarbonyl group, ethoxycarbonyl group, iso-butoxycarbonyl group, allyloxycarbonyl group, benzyloxycarbonyl group, 9-fluorenylmethoxycarbonyl group, and phenyloxycarbonyl group.

Examples of the sulfonyl group represented by $R^{3a}$ in the amide derivative of formula (Ia) are methanesulfonyl group, trifluoromethanesulfonyl group, benzenesulfonyl group, p-toluenesulfonyl group, and imidazosulfonyl group.

Examples of the substituted alkyl group represented by $R^{3a}$ in the amide derivative of formula (Ia) are benzyl group, 4-methoxybenzyl group, and 2,4-dimethoxybenzyl group.

(1) In the above-mentioned reaction schemes (B), (C) and (D), when at least one of $R^2CO$—, $R^{3a}$ or $R^3$ represents an acyl group, the deprotection can be carried out by any of the following methods (1-1), (1-2), (1-3), and (1-4) under the respective conditions:

(1-1) Solvolysis in the presence of an acid or an alkali at a temperature in the range of −10° C. to 150° C., preferably in the range of 0° C. to 120° C.

Examples of the acid for use in the solvolysis are inorganic acids such as hydrochloric acid, sulfuric acid and phosphoric acid; and organic acids such as oxalic acid, fumaric acid, maleic acid, acetic acid, trifluoroacetic acid, trichloroacetic acid, p-toluene sulfonic acid, camphor sulfonic acid, methane sulfonic acid, and trifluoromethane sulfonic acid.

Examples of the alkali for use in the solvolysis are lithium hydroxide, sodium hydroxide, potassium hydroxide, calcium oxide, barium oxide, sodium carbonate, potassium carbonate, sodium hydrogencarbonate, potassium hydrogencarbonate, sodium hydride, potassium t-butoxide, and aqueous ammonia.

Examples of a solvent for use in the solvolysis are halogenated hydrocarbons such as dichloromethane and chloroform; aromatic hydrocarbons such as benzene and toluene; ethers such as tetrahydrofuran, 1,4-dioxane, and dimethoxyethane; alcohols such as methanol, ethanol, isopropanol, n-butanol, and t-butanol; ketones such as acetone and methyl ethyl ketone; acetonitrile; dimethylformamide; dimethylacetamide; dimethylsulfoxide; and water. These solvents can be used either alone or in combination.

(1-2) Hydrazine is allowed to react with the aminobutene derivative of formula (Ia), the aminobutene derivative of formula (I), or the aminobutene derivative of formula (I-1) in water, or an alcohol such as methanol, ethanol, isopropanol, n-butanol, or t-butanol, at a temperature in the range of −10° C. to 150° C., preferably in the range of 0° C. to 120° C.

(1-3) A metal hydride such as lithium boron hydride, sodium boron hydride, or lithium aluminum hydride is allowed to react with the aminobutene derivative of formula (Ia), the aminobutene derivative of formula (I), or the aminobutene derivative of formula (I-1) in any of the following solvents, at a temperature in the range of −10° C. to 150° C., preferably in the range of 0° C. to 120° C.

Examples of the solvents for use in the above reaction are halogenated hydrocarbons such as dichloromethane and chloroform; aromatic hydrocarbons such as benzene and toluene; ethers such as tetrahydrofuran, 1,4-dioxane, and dimethoxyethane; alcohols such as methanol, ethanol, isopropanol, n-butanol, and t-butanol; acetonitrile; dimethylformamide; dimethylacetamide; dimethylsulfoxide; and water. These solvents can be used either alone or in combination.

(1-4) In the above-mentioned reaction schemes (B), (C) and (D), when at least one of $R^2CO$—, $R^{3a}$ or $R^3$ particularly represents formyl group, it is preferable that the deprotection be carried out by allowing any of the aminobutene derivative of formula (Ia), the aminobutene derivative of formula (I), and the aminobutene derivative of formula (I-1) to react with any of the following primary amines, and secondary amines in any of the following aprotic solvents, at a temperature in the range of −10° C. to 150° C., preferably in the range of 0° C. to 120° C.:

Examples of the primary amines are methylamine, ethylamine, propylamine, isopropylamine, butylamine, isobutylamine, s-butylamine, t-butylamine, cyclohexylamine, and benzylamine; examples of the secondary amines are dimethylamine, diethylamine, diisopropylamine, dicyclohexylamine, pyrrolidine, piperidine, morpholine, and piperazine.

Examples of the aprotic solvents are halogenated hydrocarbons such as dichloromethane and chloroform; aromatic hydrocarbons such as benzene and toluene; ethers such as tetrahydrofuran, 1,4-dioxane, and dimethoxyethane; ketones such as acetone and methyl ethyl ketone; acetonitrile; dimethylformamide; dimethylacetamide; and dimethylsulfoxide. These solvents can be used either alone or in combination.

Alternatively, when at least one of $R^2CO-$, $R^{3a}$ or $R^3$ particularly represents formyl group in the abovementioned reaction schemes (B), (C) and (D), the deprotection can be carried out by allowing any of the aminobutene derivative of formula (Ia), the aminobutene derivative of formula (I), and the aminobutene derivative of formula (I-1) to react with an oxidizing agent such as hydrogen peroxide in any of the following solvents at a temperature in the range of $-10°$ C. to $150°$ C., preferably in the range of $0°$ C. to $120°$ C.:

Examples of the solvents for use in the above reaction are halogenated hydrocarbons such as dichloromethane and chloroform; aromatic hydrocarbons such as benzene and toluene; ethers such as tetrahydrofuran, 1,4-dioxane, and dimethoxy-ethane; alcohols such as methanol, ethanol, isopropanol, n-butanol, and t-butanol; ketones such as acetone and methyl ethyl ketone; acetonitrile; dimethylformamide; dimethylacetamide; dimethylsulfoxide; and water. These solvents can be used either alone or in combination.

(2) In the above-mentioned reaction schemes (B), (C) and (D), when at least one of $R^2CO-$, $R^{3a}$ $R^3$ represents a sulfonyl group, the deprotection can be carried out by any of the following methods (2-1), (2-2) and (2-3) under the respective conditions:

(2-1) Solvolysis in the presence of an acid at a temperature in the range of $-10°$ C. to $150°$ C., preferably in the range of $0°$ C. to $120°$ C.

Examples of the acid for use in the solvolysis are inorganic acids such as hydrochloric acid, sulfuric acid, phosphoric acid, hydrobromic acid, and perchloric acid; and organic acids such as oxalic acid, fumaric acid, maleic acid, acetic acid, trifluoro-acetic acid, trichloroacetic acid, p-toluene sulfonic acid, camphor sulfonic acid, methane sulfonic acid, and trifluoromethane sulfonic acid.

Examples of a solvent for use in the solvolysis are halogenated hydrocarbons such as dichloromethane and chloroform; aromatic hydrocarbons such as benzene and toluene; ethers such as tetrahydrofuran, 1,4-dioxane, and dimethoxyethane; alcohols such as methanol, ethanol, isopropanol, n-butanol, and t-butanol; ketones such as acetone and methyl ethyl ketone; acetonitrile; dimethylformamide; dimethylacetamide; dimethylsulfoxide; water; and acetic acid. These solvents can be used either alone or in combination.

(2-2) An alkali metal such as lithium or sodium is allowed to react with the aminobutene derivative of formula (Ia), the aminobutene derivative of formula (I), or the aminobutene derivative of formula (I-1) in a solvent at a temperature in the range of $-78°$ C. to $100°$ C., preferably in the range of $-78°$ C. to $0°$ C.

Examples of the solvent for use in the above reaction are liquid ammonia, alcohols such as methanol, ethanol, isopropanol, n-butanol, and t-butanol; and lower amines such as methylamine, ethylamine, and ethylenediamine.

(2-3) Sodium amalgam is allowed to react with the aminobutene derivative of formula (Ia), the aminobutene derivative of formula (I), or the aminobutene derivative of formula (I-1) in a solvent at a temperature in the range of $-10°$ C. to $150°$ C., preferably in the range of $0°$ C. to $120°$ C.

Examples of the solvent for use in the above reaction are ethers such as tetrahydrofuran, 1,4-dioxane, and dimethoxyethane; alcohols such as methanol, ethanol, isopropanol, n-butanol, and t-butanol; water; and acetic acid. These solvents can be used either alone or in combination.

(3) In the above-mentioned reaction schemes (B), (C) and (D), when at least one of $R^2CO-$, $R^{3a}$ or $R^3$ represents an alkoxy-carbonyl group, the deprotection can be carried out by any of the following methods (3-1) and (3-2) under the respective conditions:

(3-1) Solvolysis in the presence of an alkali at a temperature in the range of $-10°$ C. to $150°$ C., preferably in the range of $0°$ C. to $120°$ C.

Examples of the alkali for use in the solvolysis are lithium hydroxide, sodium hydroxide, potassium hydroxide, calcium oxide, barium oxide, sodium carbonate, potassium carbonate, sodium hydrogencarbonate, potassium hydrogencarbonate, sodium hydride, potassium t-butoxide, and aqueous ammonia.

Examples of the solvent for use in the solvolysis are halogenated hydrocarbons such as dichloromethane and chloroform; aromatic hydrocarbons such as benzene and toluene; ethers such as tetrahydrofuran, 1,4-dioxane, and dimethoxyethane; alcohols such as methanol, ethanol, isopropanol, n-butanol, and t-butanol; ketones such as acetone and methyl ethyl ketone; acetonitrile; dimethylformamide; dimethylacetamide; dimethylsulfoxide; and water. These solvents can be used either alone or in combination.

(3-2) Solvolysis in the presence of an acid at a temperature in the range of $-10°$ C. to $150°$ C., preferably in the range of $0°$ C. to $120°$ C., if necessary in the presence of a scavenger:

Examples of the acid for use in the solvolysis are inorganic acids such as hydrochloric acid, sulfuric acid and phosphoric acid; and organic acids such as oxalic acid, fumaric acid, maleic acid, acetic acid, trifluoroacetic acid, trichloroacetic acid, p-toluene sulfonic acid, camphor sulfonic acid, methane sulfonic acid, and trifluoromethane sulfonic acid; Lewis acids such as aluminum chloride, zinc chloride, magnesium bromide, stannic chloride, titanium tetrachloride, and boron trifluoride.

Examples of the solvent for use in the solvolysis are halogenated hydrocarbons such as dichloromethane and chloroform; aromatic hydrocarbons such as benzene and toluene; ethers such as tetrahydrofuran, 1,4-dioxane, and dimethoxyethane; alcohols such as methanol, ethanol, isopropanol, n-butanol, and t-butanol; ketones such as acetone and methyl ethyl ketone; acetonitrile; dimethylformamide; dimethylacetamide; dimethylsulfoxide; and water. These solvents can be used either alone or in combination. Examples of the scavenger for use in the above solvolysis are phenol, thiophenol, anisole, thioanisole, cresol, thiocresol, and dimethylsulfide.

(4) In the above-mentioned reaction schemes (B), (C) and (D), when at least one of $R^2CO-$, $R^{3a}$ $R^3$ or represents a substituted alkyl group, the deprotection can be carried out by any of the following methods (4-1) and (4-2) under the respective conditions:

(4-1) Solvolysis in the presence of an acid, or the direct reaction with an acid without using any solvents, at a temperature in the range of $-10°$ C. to $150°$ C., preferably in the range of $0°$ C. to $120°$ C.

Examples of the acid for use in the solvolysis are inorganic acids such as hydrochloric acid, sulfuric acid and phosphoric acid; and organic acids such as oxalic acid, fumaric acid, maleic acid, acetic acid, trifluoroacetic acid, trichloroacetic acid, p-toluene sulfonic acid, camphor sulfonic acid, methane sulfonic acid, and trifluoromethane sulfonic acid.

Examples of a solvent for use in the above solvolysis are halogenated hydrocarbons such as dichloromethane and chloroform; aromatic hydrocarbons such as benzene and toluene; ethers such as tetrahydrofuran, 1,4-dioxane, and dimethoxyethane; alcohols such as methanol, ethanol, isopropanol, n-butanol, and t-butanol; ketones such as acetone and methyl ethyl ketone; acetonitrile; dimethyl-formamide; dimethylacetamide; dimethylsulfoxide; and water. These solvents can be used either alone or in combination.

(4-2) An oxidizing agent, such as 2,3-dichloro-5,6-dicyano-1,4-benzoquinone (DDQ), tetrachloro-1,2-benzoquinone, or tetrachloro-1,4-benzoquinone, is allowed to react with the aminobutene derivative of formula (Ia), the aminobutene derivative of formula (I), or the aminobutene derivative of formula (I-1) in any of the following solvents at a temperature in the range of $-10°$ C. to 150° C., preferably in the range of 0° C. to 120° C.:

Examples of the solvent for use in the above oxidation reaction are halogenated hydrocarbons such as dichloromethane and chloroform; aromatic hydrocarbons such as benzene and toluene; ethers such as tetrahydrofuran, 1,4-dioxane, and dimethoxyethane; alcohols such as methanol, ethanol, isopropanol, n-butanol, and t-butanol; ketones such as acetone and methyl ethyl ketone; acetonitrile; dimethylformamide; dimethylacetamide; dimethylsulfoxide; and water. These solvents can be used either alone or in combination.

Specifically, the pyridyloxy derivative of formula (I-3) can be prepared by carrying out the above-mentioned deprotection of the previously mentioned acetimide derivative of formula (I-4) in accordance with the following reaction scheme:

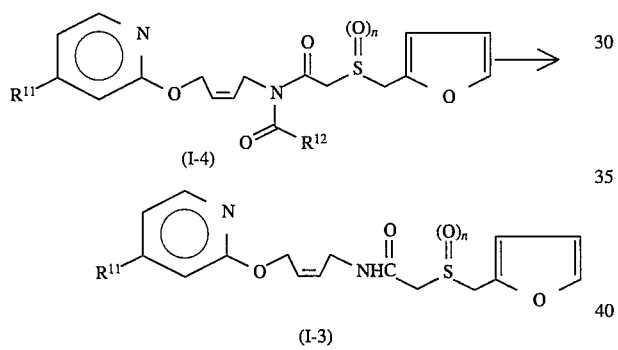

wherein $R^{11}$ and $R^{12}$ are respectively the same as defined previously, and n is an integer of 0, 1 or 2.

In the pyridyloxy derivative of formula (I-2), when n is an integer of 0 or 1, a pyridyloxy derivative of the formula (I-3a) can be prepared by oxidizing the pyridyl derivative of formula (I-2):

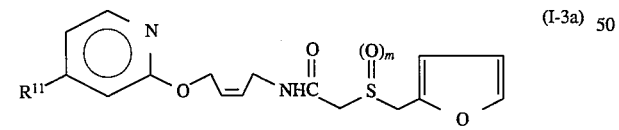

wherein $R^{11}$ is the same as in the above formula (I-2), and m is n+1 in which n is 0 or 1.

According to the present invention, when $R^1$ is a protective group for hydroxyl group in the aminobutene derivative of formula (Ia), the aminobutene derivative of formula (I), or the aminobutene derivative of formula (I-1), aminobutenol of formula (A), can be prepared by subjecting any of the aminobutene derivative of formula (Ia), the aminobutene derivative of formula (I), and the aminobutene derivative of formula (I-1) to deprotection by any of the following methods (A-1), (A-2), and (A-3):

(A-1) Solvolysis in the presence of an acid or an alkali at a temperature in the range of $-10°$ C. to 150° C., preferably at a temperature in the range of 0° C. to 120° C., provided that in the solvolysis in the presence of an acid, the solvolysis may be carried out in the presence of a scavenger if necessary.

Examples of the acid for use in the solvolysis are inorganic acids such as hydrochloric acid, sulfuric acid and phosphoric acid; and organic acids such as oxalic acid, fumaric acid, maleic acid, acetic acid, trifluoroacetic acid, trichloroacetic acid, p-toluene sulfonic acid, camphor sulfonic acid, methane sulfonic acid, and trifluoromethane sulfonic acid; Lewis acids such as aluminum chloride, zinc chloride, magnesium bromide, stannic chloride, titanium tetrachloride, and boron trifluoride.

Examples of the alkali for use in the above solvolysis are lithium hydroxide, sodium hydroxide, potassium hydroxide, calcium oxide, barium oxide, sodium carbonate, potassium carbonate, sodium hydrogencarbonate, potassium hydrogencarbonate, sodium hydride, potassium t-butoxide, and aqueous ammonia.

Examples of a solvent for use in the solvolysis are halogenated hydrocarbons such as dichloromethane and chloroform; aromatic hydrocarbons such as benzene and toluene; ethers such as tetrahydrofuran, 1,4-dioxane, and dimethoxyethane; alcohols such as methanol, ethanol, isopropanol, n-butanol, and t-butanol; ketones such as acetone and methyl ethyl ketone; acetonitrile; dimethylformamide; dimethylacetamide; dimethylsulfoxide; and water. These solvents can be used either alone or in combination.

Examples of the scavenger for use in the above solvolysis are phenol, thiophenol, anisole, thioanisole, cresol, thiocresol, and dimethylsulfide.

(A-2) Hydrazine is allowed to react with the aminobutene derivative of formula (Ia), the aminobutene derivative of formula (I), or the aminobutene derivative of formula (I-1) in water, or an alcohol such as methanol, ethanol, isopropanol, n-butanol, or t-butanol, at a temperature in the range of $-10°$ C. to 150° C., preferably in the range of 0° C. to 120° C.

(A-3) A fluoride such as sodium fluoride, potassium fluoride, tetrabutylammonium fluoride, boron fluoride, or hydrogen fluoride is allowed to react with the aminobutene derivative of formula (Ia), the aminobutene derivative of formula (I), or the aminobutene derivative of formula (I-1) in any of the following solvents, at a temperature in the range of $-10°$ C. to 150° C., preferably in the range of 0° C. to 120° C.

Examples of the solvent for use in the above reaction are halogenated hydrocarbons such as dichloromethane and chloroform; aromatic hydrocarbons such as benzene and toluene; ethers such as tetrahydrofuran, 1,4-dioxane, and dimethoxyethane; alcohols such as methanol, ethanol, isopropanol, n-butanol, and t-butanol; ketones such as acetone and methyl ethyl ketone; acetonitrile; dimethylformamide; dimethyiacetamide; dimethylsulfoxide; and water. These solvents can used either alone or in combination.

Other features of this invention will become apparent in the course of the following description of exemplary embodiments, which are given for illustration of the invention and are not intended to be limiting thereof.

REFERENCE EXAMPLE 1

Synthesis of (Z)-4-piperidinomethyl-2-(4-tetrahydropyranyloxgy-2-butenyloxy)-pyridine:

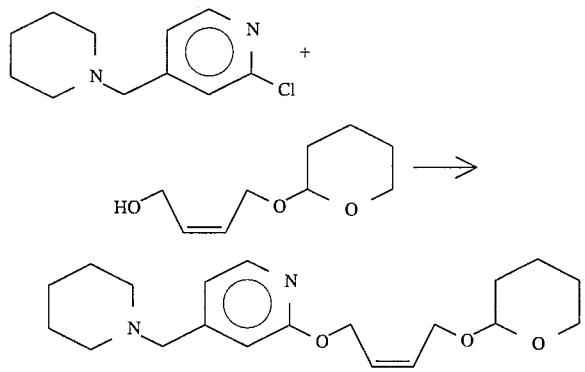

1.10 g (0.025 mol) of sodium hydride was suspended in 20 ml of THF. 10 ml of a THF solution containing 4.31 g (0.025 mol) of (Z)-4-tetrahydropyranyloxy-2-butenol was added dropwise to the above suspension at room temperature, and the mixture was stirred for 20 minutes.

10 ml of a THF solution containing 2.10 g (0.01 mol) of 2-chloro-4-piperidinomethylpyridine and 2 ml of DMF were successively added to the above mixture, and the mixture was refluxed for 16 hours. After the completion of the reaction, the solvent was distilled away from the reaction mixture. A residue thus obtained was added to chloroform and extracted with 1N hydrochloric acid. A resultant aqueous layer was made basic by the addition of anhydrous potassium carbonate, and extracted with chloroform. A resultant organic extract layer was washed with brine, and dried. The solvent was distilled away from the organic extract, so that (Z)-4-piperidinomethyl-2-(4-tetrahydropyranyloxy-2-butenyl-oxy)pyridine was obtained in a yield of 3.10 g (89%).

$^1$H-NMR (δ, CDCl$_3$): 1.40–1.95 (8H, m), 2.35–2.55 (4H, m), 3.47 (2H, s), 3.50–3.58 (1H, m), 3.95–4.05 (1H, m), 4.33 (2H, dd, J=6 Hz), 4.90 (1H, br-t, J=2 Hz), 4.99 (2H, d, J=7 Hz), 5.68–5.78 (1H, m), 5.84–5.94 (1H, m), 6.77 (1H, s), 6.94 (1H, d, J=5 Hz), 8.02 (1H, d, J=5 Hz)

REFERENCE EXAMPLE 2

Synthesis of (Z)-4-[4-(piperidinomethyl)pyridyl-2-oxy]-2-butenol:

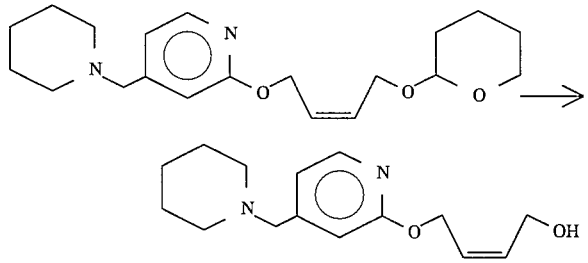

5.0 g (0.014 mol) of (Z)-4-piperidinomethyl-2-(4-tetrahydropyranyloxy-2-butenyloxy)pyridine was dissolved in 60 ml of methanol. 6.0 g (0.032 mol) of p-toluenesulfonic acid•monohydrate was added to the above mixture under an ice-cooled condition, and the mixture was stirred for 2 hours.

The thus obtained mixture was made basic by the addition of a saturated aqueous solution of sodium bicarbonate. The reaction mixture was concentrated with the elimination of the solvent therefrom, and extracted with ethyl acetate. A resultant organic extract layer was washed with brine, and dried. The solvent was distilled away from the organic extract, and the residue thus obtained was chromatographed on a silica gel column, so that (Z)-4-[4-(piperidinomethyl)pyridyl-2-oxy]-2-butenol was obtained in a yield of 3.1 g (82%).

Boiling Point: 177°–179° C./2 mmHg $^1$H-NMR (δ, CDCl$_3$): 1.40–1.55 (2H, m), 1.55–1.70 (4H, m), 2.35–2.55 (4H, m), 3.47 (2H, s), 3.90 (1H, br-s), 4.33 (2H, dd, J=5 Hz), 5.00 (2H, d, J=7 Hz), 5.70–5.80 (1H, m), 5.84–5.94 (1H, m), 6.76 (1H, s), 6.93 (1H, d, J=5 Hz), 8.02 (1H, d, J=5 Hz)

The above obtained compound was purified in the form of the oxalate.

Melting Point: 123.4°–124.4° C.

The results of the elemental analysis of the above compound were as follows:

|        | % C   | % H  | % N  |
|--------|-------|------|------|
| Calcd. | 57.94 | 6.87 | 7.95 |
| Found  | 58.09 | 7.03 | 8.14 |

The above calculation was based on the formula for (Z)-4-[4-(piperidinomethyl)pyridyl-2-oxy]-2-butenol of $C_{17}H_{24}N_2O_6$.

REFERENCE EXAMPLE 3

Synthesis of 2-furfurylthioacetamide:

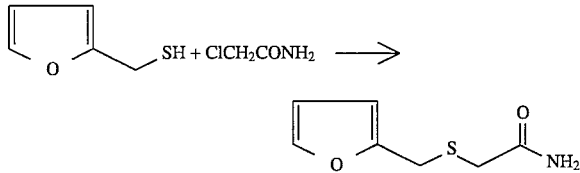

11.4 g (0.1 mol) of 2-furfuryl mercaptan and 9.4 g (0.1 mol) of 2-chloroacetamide were dissolved in 100 ml of acetonitrile. With the addition of 13.8 g (0.1 mol) of anhydrous potassium carbonate, the above solution was refluxed for 3 hours.

After the completion of the reaction, the solvent was distilled away. A thus obtained residue was added to ethyl acetate, and washed successively with water three times and with brine. A resultant organic extract layer was dried, and the solvent was distilled away therefrom. The thus obtained residue was recrystallized from a mixed solvent of hexane and ethyl acetate, so that 2-furfurylthioacetoamide was obtained in a yield of 16.4 g (96%).

Melting Point: 66.9°–67.6° C. (recrystallized from a mixed solvent of hexane and ethyl acetate with a ratio of 1:1)

$^1$H-NMR (δ, CDCl$_3$): 3.21 (2H, s), 3.79 (2H, s), 5.90–6.15 (1H, br), 6.23 (1H, d, J=3 Hz), 6.32 (1H, dd, J=3.2 Hz), 6.45–6.80 (1H, br), 7.37 (1H, d, J=2 Hz)

IR (ν, KBr): 3400, 3280, 1640, 1505, 1410, 1400, 1385, 1260, 1225, 1150, 1005, 940, 745 cm$^{-1}$

The results of the elemental analysis of the above compound were as follows:

|  | % C | % H | % N | % S |
| --- | --- | --- | --- | --- |
| Calcd. | 49.10 | 5.30 | 8.18 | 18.73 |
| Found | 49.10 | 5.30 | 8.24 | 18.96 |

The above calculation was based on the formula for 2-furfurylthioacetamide of $C_7H_9NO_2S$.

REFERENCE EXAMPLE 4

Synthesis of 2-furfurylsulfinylacetamide:

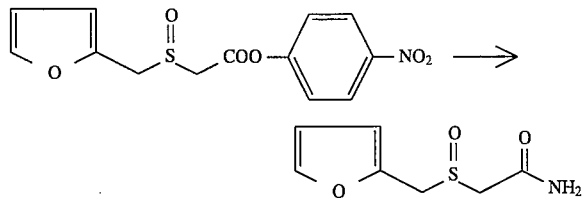

3.1 g (10 mmol) of p-nitrophenyl 2-furfurylsulfinyl acetate was suspended in 30 ml of ethanol. To the above suspension, 20 ml of a 28% aqueous ammonia was added, and the mixture was refluxed for an hour. After the completion of the reaction, the solvent was distilled away from the reaction mixture. A residue thus obtained was recrystallized from ethyl acetate, so that 2-furfurylsulfinylacetamide was obtained in a yield of 1.2 g (64%)

Melting Point: 144.6°–145.3° C.

$^1$H-NMR (δ, CDCl$_3$): 3.30 (1H, d, J=15 Hz), 3.62 (1H, d, J=15 Hz), 4.22 (1H, d, J=14 Hz), 4.26 (1H, d, J=14 Hz), 5.48–5.66 (1H, br), 6.41 (1H, dd, J=4.2 Hz), 6.48 (1H, d, J=4 Hz), 6.84–6.96 (1H, m), 7.45 (1H, d, J=2 Hz)

REFERENCE EXAMPLE 5

Synthesis of N-acetyl-2-furfurylthioacetamide:

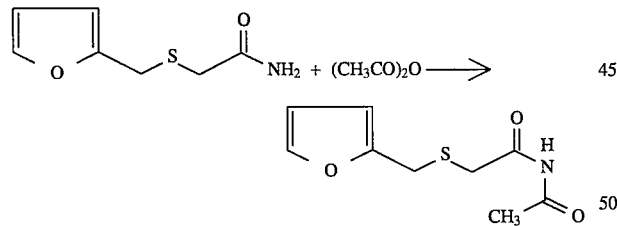

8.56 g (0.05 mol) of 2-furfurylthioacetamide, 5.61 g (0.055 mol) of acetic anhydride, and 6.11 g (0.05 mol) of N,N-dimethyl-aminopyridine were dissolved in 50 ml of pyridine. The mixture was stirred at 80° C. for 16 hours. The solvent was distilled away from the reaction mixture, and the residue thus obtained was added to ethyl acetate and washed successively with water, 1N hydrochloric acid, water three times, and brine. A resultant organic extract layer was dried, and the solvent was distilled away therefrom, so that N-acetyl-2-furfurylthioacetamide was obtained in a yield of 7.11 g (60%).

$^1$H-NMR (δ, CDCl$_3$): 2.35 (3H, s), 3.36 (2H, s), 3.79 (2H, s), 6.22 (1H, d, J=3 Hz), 6.30 (1H, dd, J=3.2 Hz), 7.36 (1H, d, J=2 Hz), 8.70–8.95 (1H, br-s)

REFERENCE EXAMPLE 6

Synthesis of N-formyl-2-furfurylthioacetamide:

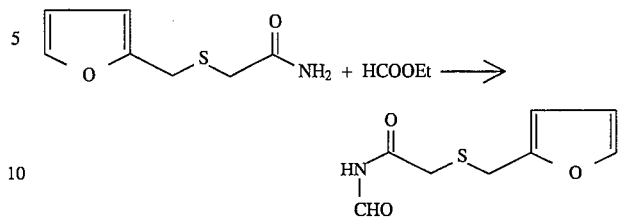

0.768 g (19.2 mmol) of a 60% oily sodium hydride was suspended in 50 ml of THF. To the above suspension, 100 ml of a THF solution containing 3 g (17.4 mmol) of 2-furfurylthioacetamide was added dropwise under an ice-cooled condition, and the mixture was stirred at room temperature for 30 minutes.

After the addition of 1.54 ml (19.2 mmol) of ethyl formate under an ice-cooled condition, the above obtained mixture was further stirred at room temperature for 2 hours. With the addition of 1.1 ml (19.2 mmol) of acetic acid, the thus obtained reaction mixture was stirred at room temperature for 10 minutes and concentrated under reduced pressure.

A residue thus obtained was dissolved in a mixture of 150 ml of ethyl acetate and 50 ml of water, whereby an organic layer was separated therefrom. The thus obtained organic layer was washed with brine, dried over anhydrous sodium sulfate, and concentrated under reduced pressure.

A residue thus obtained was chromatographed on a silica gel column, so that N-formyl-2-furfurylthioacetoamide was obtained in a yield of 2.4 g (69%).

Melting Point: 51.0°–52.1° C. (recrystallized from a mixed solvent of ethyl acetate and hexane)

$^1$H-NMR (δ, CDCl$_3$): 3.32 (2H, 5), 3.79 (2H, s), 6.23 (1H, d, J=3 Hz), 6.31 (1H, m), 7.36 (1H, d, J=2 Hz), 8.80–9.10 (1H, br), 8.98 (1H, br)

IR (ν, KBr): 3224, 3180, 1734, 1684, 1478, 1384, 1258, 1234, 750 cm$^{-1}$

REFERENCE EXAMPLE 7

Synthesis of N-benzoyl-2-furfurylthioacetamide:

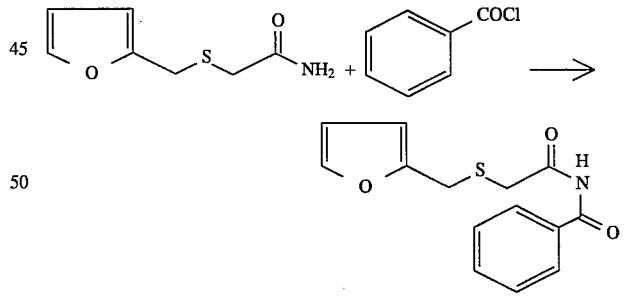

12.11 g (0.07 mol) of 2-furfurylthioacetamide was dissolved in 30 ml of pyridine. To the above solution, 9.94 g (0.07 mol) of benzoylchloride was added, and the mixture was stirred at 60° C. for 15 hours. The solvent was distilled away from the reaction mixture, and a residue thus obtained was added to ethyl acetate and washed successively with water twice, 1N hydrochloric acid, water three times, and brine. A resultant organic extract layer was dried, and the solvent was distilled away therefrom.

A residue thus obtained was chromatographed on a silica gel column for purification, so that N-benzoyl-2-furfurylthioacetamide was obtained in a yield of 14.2 g (73%).

¹H-NMR (δ, CDCl₃): 3.22 (2H, s), 3.94 (2H, s), 6.30 (1H, d, J=3 Hz), 6.35 (1H, dd, J=3.2 Hz), 7.40 (1H, d, J=2 Hz), 7.48 (2H, dd, J=7.7 hz), 7.62 (1H, dd, J=7.7 Hz), 8.12 (2H, d, J=7 Hz), 8.40–8.90 (1H, br)

REFERENCE EXAMPLE 8

Synthesis of N-t-butoxycarbonyl-2-furfurylthioacetamide:

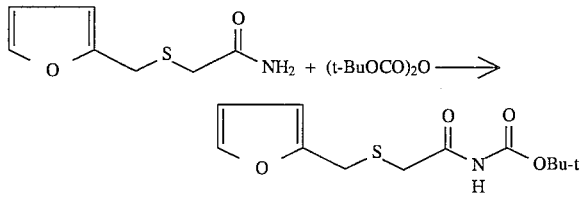

1.68 g (42.0 mol) of a 60% oily sodium hydride was suspended in 50 ml of THF. To the above suspension, 50 ml of a THF solution containing 3.00 g (17.5 mmol) of 2-furfurylthioacetamide was added dropwise under an ice-cooled condition. The mixture was stirred at room temperature for 20 minutes. With the dropwise addition of 4.8 ml (21 mmol) of di-t-butyldicarbonate, the above mixture was further stirred at room temperature for 4 hours. The solvent was distilled away from the above mixture, and a residue thus obtained was dissolved in water, neutralized by the addition of 1N hydrochloric acid, and extracted with ethyl acetate.

A resultant organic extract layer was washed with brine, dried over anhydrous sodium sulfate. The solvent was distilled away under reduced pressure from the organic extract. A residue thus obtained was recrystallized from a mixed solvent of chloroform and hexane, so that N-t-butoxy-carbonyl-2-furfurylthioacetamide was obtained in a yield of 4.08 g (86%).

Melting Point: 106.6°–108.7° C.

¹H-NMR (δ, CDCl₃): 1.49 (9H, s), 3.52 (2H, s), 3.80 (2H, s), 6.25 (1H, d, J=2.8 Hz), 6.31 (1H, dd, J=5.0, 1.9 Hz), 7.36 (1H, d, J=2.0 Hz), 7.75 (1H, br-s)

IR (ν, KBr): 3272, 1750, 1692, 1532 cm⁻¹

REFERENCE EXAMPLE 9

Synthesis of N-methoxycarbonyl-2-furfurylthioacetoamide:

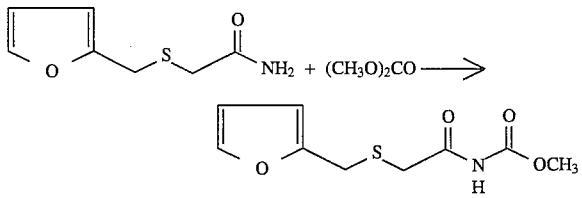

1.29 g (0.032 mol) of a 60% oily sodium hydride was suspended in 20 ml of THF. To the above suspension, 50 ml of a THF solution containing 5 g (0.029 mol) of 2-furfurylthioacetamide was added dropwise under an ice-cooled condition, and the mixture was stirred at room temperature for 30 minutes. With the dropwise addition of 2.7 ml (0.032 mol) of dimethylcarbonate under an ice-cooled condition, the above mixture was further stirred for 30 minutes. The solvent was distilled away under reduced pressure from the above reaction mixture, and a residue thus obtained was dissolved in water, neutralized by the addition of 1N hydrochloric acid, and extracted with ethyl acetate.

A resultant organic extract layer was washed with brine, dried over anhydrous sodium sulfate. The solvent was distilled away under reduced pressure from the organic extract layer. A residue thus obtained was recrystallized from toluene, so that N-methoxycarbonyl-2-furfurylthioacetamide was obtained in a yield of 2.78 g (42%).

Melting Point: 120.0°–121.5° C.

¹H-NMR (δ, CDCl₃): 3.55 (2H, s), 3.79 (3H, s), 3.80 (2H, s), 6.25 (1H, d, J=2.9 Hz), 6.31 (1H, dd, J=2.0, 2.9 Hz), 7.37 (1H, d, J=2.0 Hz), 7.86 (1H, br s)

IR (ν, KBr): 3260, 3196, 1760, 1532 cm⁻¹

REFERENCE EXAMPLE 10

Synthesis of N-2,4-dimethoxybenzyl-2-(furfurylthio)acetamide:

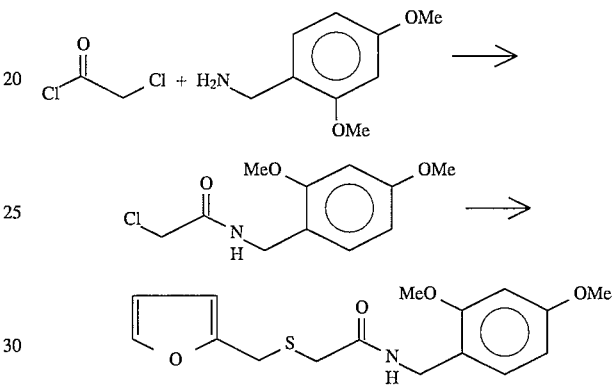

30 ml of an ethyl acetate solution containing 3 g of chloroacetyl chloride was mixed with 30 ml of an aqueous solution containing 7.35 g of potassium carbonate. To this mixture, 10 ml of an ethyl acetate solution containing 5.41 g of 2,4-dimethoxybenzylamine was added dropwise, and the mixture was stirred for one hour.

After the completion of the reaction, the reaction mixture was washed successively with water and brine. A resultant organic layer was dried, and the solvent was distilled away therefrom. A residue thus obtained was dissolved in 50 ml of acetonitrile. With the addition of 3 g of furfuryl mercaptan and 3.7 g of anhydrous potassium carbonate, the mixture was refluxed for three hours. After the completion of the reaction, the solvent was distilled away from the reaction mixture. A residue thus obtained was added to ethyl acetate, and washed successively with water and brine. A resultant organic layer was dried, and the solvent was distilled away therefrom. A residue thus obtained was chromatographed on a silica gel column, so that N-2,4-dimethoxybenzyl-2-(furfurylthio)acetamide was obtained in a yield of 6.9 g (90%).

¹H-NMR (δ, CDCl₃): 3.19 (2H, s), 3.68 (2H, s), 3.80 (3H, s), 3.84 (3H, s), 4.34 (2H, d, J=6 Hz), 6.15 (1H, d, J=3 Hz), 6.26 (1H, dd, J=3 Hz, J=2 Hz), 6.40–6.50 (2H, m), 7.15 (1H, br-s), 7.16 (1H, d, J=8 Hz), 7.28 (1H, d, J=2 Hz)

EXAMPLE 1

Synthesis of (Z)-4-amino-2-butene-1-ol•p-toluenesulfonate:

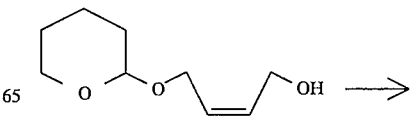

-continued

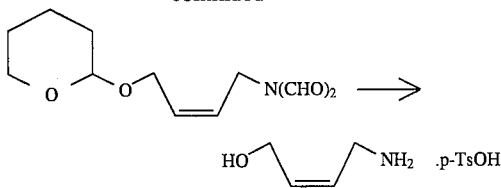

(1) Synthesis of (Z)-N,N-diformyl-1-amino-4-tetrahydropyranyl-2-oxy)-2-butene:

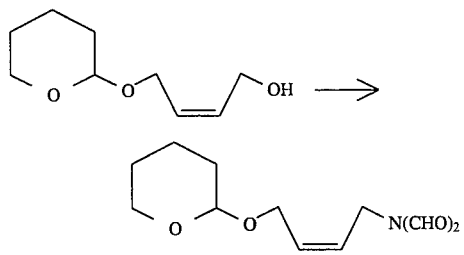

10.3 g (90 mmol) of methanesulfonylchloride was added dropwise to 200 ml of an ethyl acetate solution containing 10.33 g (60 mmol) of (Z)-4-(tetrahydropyranyl-2-oxy)-2-butene-1-ol and 9.1 g (90 mmol) of triethylamine under an ice-cooled condition. The mixture was stirred for 2 hours.

The thus obtained reaction mixture was washed successively with 1N hydrochloric acid, a 1N sodium hydroxide aqueous solution and brine, and dried over anhydrous sodium sulfate.

The solvent was distilled away under reduced pressure from the above reaction mixture. A residue thus obtained was dissolved in 100 ml of acetonitrile, and 7.6 g (80 mmol) of sodium diformylamide synthesized in accordance with the method described in Synthesis, 1982, 264 was added thereto. The above mixture was then refluxed for 2 hours, and cooled to room temperature.

Insolubles were removed from the above mixture by filtration. A filtrate was concentrated under reduced pressure, so that (Z)-N,N-diformyl-1-amino-4-(tetrahydropyranyl-2-oxy)-2-butene was obtained in a yield of 11.99 g (88%).

$^1$H-NMR (δ, CDCl$_3$): 1.45–1.90 (m, 6H), 3.50–3.60 (m, 1H), 3.80–3.95 (m, 1H), 4.25 (dd, J=12 Hz, 7 Hz, 1H), 4.32 (d, J=7 Hz, 2H), 4.40 (dd, J=12 Hz, 5 Hz, 1H), 4.67 (t, J=3 Hz, 1H), 5.45–5.55 (m, 1H), 5.70–5.85 (m, 1H), 8.84 (s, 2H)

(2) Synthesis of (Z)-4-amino-2-butene-1-ol•p-toluene sulfonate:

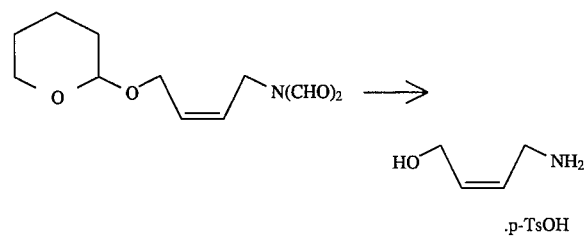

9.89 g (52 mmol) of p-toluene sulfonic acid•monohydrate was added to 300 ml of a methanol solution containing 11.99 g (52 mmol) of the above obtained (Z)-N,N-diformyl-1-amino-4-(tetrahydro-pyranyl-2-oxy)-2-butene, and the mixture was stirred at room temperature for 18 hours. The reaction mixture was then concentrated under reduced pressure, so that (Z)-4-amino-2-butene-1-ol•p-toluenesulfonate was obtained in a yield of 80%.

$^1$H-NMR (δ, CD$_3$OD): 2.36 (s, 3H), 3.64 (d, J=7 Hz, 2H), 4.19 (d, J=7 Hz, 2H), 5.55–5.65 (m, 1H), 5.85–6.00 (m, 1H), 7.24 (d, J=8 Hz, 2H), 7.70 (d, J=8 Hz, 2H)

EXAMPLE 2

Synthesis of (Z)-4-amino-2-butene-1-ol•hydrochloride:

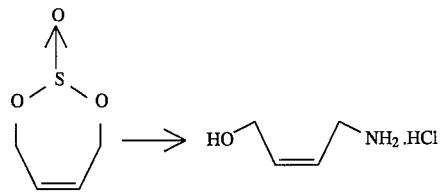

1.04 g (11 mmol) of sodium diformylamide and 0.339 g (1 mmol) of tetrabutylammonium hydrogensulfate were added to 50 ml of a toluene solution containing 1.34 g (10 mmol) of 4,7-dihydro-1,3,2-dioxathiepin-2-oxide synthesized in accordance with the method described in Chemica Scripta vol 124, 170–177, (1984), and the mixture was refluxed for 2 hours.

The above reaction mixture was cooled to room temperature, and the solvent was distilled away therefrom. A residue thus obtained was dissolved in 50 ml of ethanol. With the addition of 10 ml of 12N hydrochloric acid, the reaction mixture was refluxed for 3 hours, cooled to room temperature, and concentrated under reduced pressure, so that (Z)-4-amino-2-butene-1-ol•hydrochloride was obtained in a yield of 0.537 g (50%).

$^1$H-NMR (δ, CD$_3$OD): 3.64 (d, J=7 Hz, 2H), 4.19 (d, J=7 Hz, 2H), 5.55–5.65 (m, 1H), 5.85–5.75 (m, 1H)

EXAMPLE 3

Synthesis of (Z)-4-amino-2-butene-1-ol•p-toluenesulfonate:

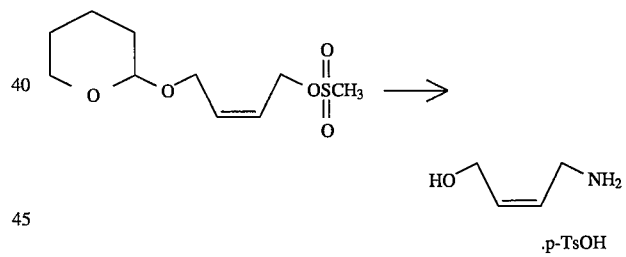

15.35 ml (80 mmol) of a 28% methanol solution of sodium methoxide was added to 40 ml of formamide, and the mixture was stirred at room temperature for 10 minutes. The above mixture was then heated to 90° C. for one hour, and the methanol was distilled away. To the thus obtained reaction mixture, 50 ml of a THF solution containing 15.01 g (60 mmol) of (Z)-4-(tetrahydropyranyl-2-oxy)-2-butene-1-ol•methane sulfonate was added dropwise, and the mixture was stirred for 2 hours. The above reaction mixture was stirred at room temperature for 18 hours. Subsequently, the reaction mixture was added to iced water, and extracted with methylene chloride twice. A resultant organic extract layer was washed with brine, dried over anhydrous sodium sulfate, and concentrated under reduced pressure, whereby 15.1 g of a mixture of (Z)-N,N-diformyl-1-amino-4-(tetrahydropyranyl-2-oxy)-2-butene and (Z)-N-formyl-1-amino-4-(tetrahydro-pyranyl-2-oxy)-2-butene was obtained.

11.41 g (60 mmol) of p-toluene sulfonic acid•monohydrate was added to 300 ml of a methanol solution of the above obtained mixture, and the reaction mixture was stirred for 18 hours, and concentrated under reduced pressure, so that 13.53 g of (Z)-4-amino-2-butene-1-ol•p-toluene sulfonate was obtained. The yield of the above obtained compound was 87%, which was calculated from the amount of the employed (Z)-(4-tetrahydropyranyl-2-oxy)-2-butene-1-ol•methane sulfonate.

$^1$H-NMR (δ, CD$_3$OD): 2.36 (s, 3H), 3.64 (d, J=7 Hz, 2H), 4.19 (d, J=7 Hz, 2H), 5.55–5.65 (m, 1H), 5.85–6.00 (m, 1H), 7.24 (d, J=8 Hz, 2H), 7.70 (d, J=8 Hz, 2H)

EXAMPLE 4

Synthesis of (Z)-N-[4-[4-(piperidinomethyl)pyridyl-2-oxy]-2-butenyl]acetamide:

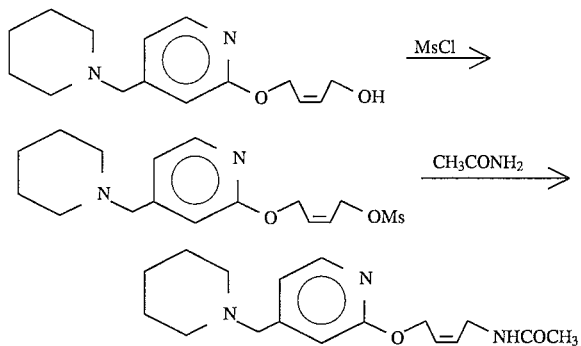

523 mg (2 mmol) of (Z)-N-4[4-(piperidinomethyl)pyridyl-2-oxy]-2-butenol and 252 mg (2.5 mmol) of triethylamine were dissolved in 10 ml of toluene. To the above solution, 2 ml of a toluene solution containing 286 mg (2.4 mmol) of methanesulfonyl chloride was added dropwise at room temperature, and the mixture was stirred for one hour.

After the completion of the reaction, a precipitate was separated from the reaction mixture by filtration to obtain a flitrate. The precipitate thus obtained in the form of a solid was washed with 10 ml of toluene to obtain washings, and the washings were added to the above obtained filtrate.

132 mg (2.2 mmol) of acetamide was dissolved in 10 ml of THF, and 247 mg (2.2 mmol) of potassium t-butoxide was added thereto at room temperature. The thus obtained mixture was stirred for one hour. To this mixture, the previously prepared reaction mixture of the washings and the filtrate was added dropwise at room temperature. After the addition of 68 mg (0.2 mmol) of tetra-n-butyl-ammonium hydrogensulfate, the thus obtained reaction mixture was stirred for one hour, washed successively with water three times and brine, and dried. The solvent was distilled away from the reaction mixture, and a residue thus obtained was chromatographed on a silica gel column, so that (Z)-N-[4-[4-(piperidinomethyl)pyridyl-2-oxy]-2-butenyl]acetamide was obtained in a yield of 490 mg (81%).

$^1$H-NMR (δ, CDCl$_3$): 1.40–1.50 (2H, m), 1.55–1.68 (4H, m), 2.00 (3H, s), 2.30–2.48 (4H, m), 3.44 (2H, s), 4.03 (2H, t, J=6 Hz), 4.93 (2H, d, J=7 Hz), 5.65–5.75 (1H, m), 5.77–5.87 (1H, m), 6.02–6.16 (1H, br-s), 6.75 (1H, s), 6.91 (1H, d, J=5 Hz), 8.05 (1H, d, J=5 Hz)

IR (ν, film): 2940, 1658, 1614, 1564, 1424, 1288, 1164, 1148, 1114, 1038, 998 cm$^{-1}$

EXAMPLE 5

Synthesis of (Z)-N-[4-[4-(piperidinomethyl)pyridyl-2-oxy]-2-butenyl]formamide:

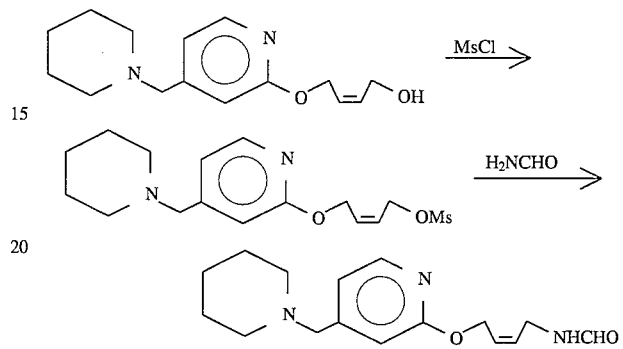

523 mg (2 mmol) of (Z)-N-4[4-(piperidinomethyl)pyridyl-2-oxy]-2-butenol and 252 mg (2.5 mmol) of triethylamine were dissolved in 10 ml of toluene. To the above solution, 2 ml of a toluene solution containing 286 mg (2.4 mmol) of methane sulfonylchloride was added dropwise at room temperature, and the mixture was stirred for one hour. After the completion of the reaction, a precipitate was separated from the above reaction mixture by filtration to obtain a filtrate. The thus obtained precipitate in the form of a solid was washed with 10 ml of toluene to obtain washings, and the washings were added to the above obtained filtrate.

132 mg (2.2 mmol) of formamide was dissolved in 10 ml of THF, and 247 mg (2.2 mmol) of potassium t-butoxide was added thereto at room temperature. The above mixture was then stirred for one hour. To this mixture, the previously prepared reaction mixture of the washings and the filtrate was added dropwise at room temperature, followed by the addition of 68 mg (0.2 mmol) of tetra-n-butylammonium hydrogensulfate. The thus obtained reaction mixture was stirred for 2 hours, washed successively with water three times and with brine, and dried. The solvent was distilled away from the reaction mixture, and a residue thus obtained was chromatographed on a silica gel column, so that (Z)-N-[4-[4-(piperidinomethyl)pyridyl-2-oxy]-2-butenyl]formamide was obtained in a yield of 220 mg (38%).

$^1$H-NMR (δ, CDCl$_3$): 1.38–1.52 (2H, m), 1.52–1.74 (4H, m), 2.30–2.72 (4H, m), 3.49 (2H, s), 4.09 (2H, dd, J=6.6 Hz), 4.94 (2H, d, J=6 Hz), 5.64–5.78 (1H, m), 5.80–5.92 (1H, m), 6.24–6.40 (1H, m), 6.79 (1H, s), 6.95 (1H, d, J=5 Hz), 8.05 (1H, d, J=5 Hz), 8.22 (1H, s)

IR (ν, film): 2936, 1668, 1614, 1562, 1424, 1404, 1314, 1164, 1148, 1038, 996 cm$^{-1}$

EXAMPLE 6

Synthesis of (Z)-N-[4-[4-(piperidinomethyl)pyridyl-2-oxy]-2-butenyl]benzamide:

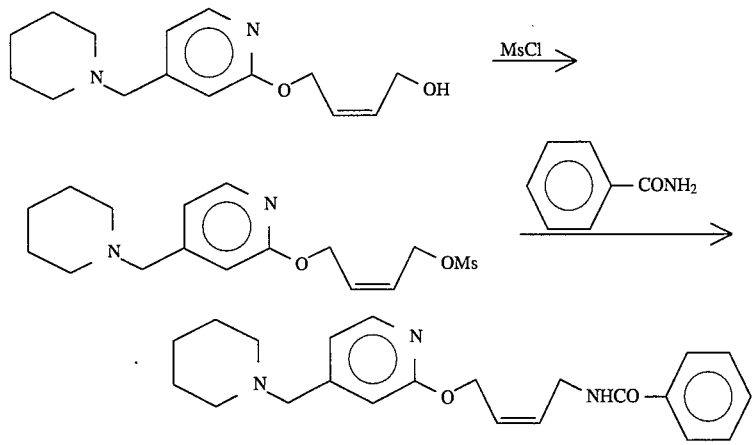

523 mg (2 mmol) of (Z)-N-4-[4-(piperidinomethyl)-pyridyl-2-oxy]-2-butenol and 252 mg (2.5 mmol) of triethylamine were dissolved in 10 ml of toluene. To this solution, 2 ml of a toluene solution containing 286 mg (2.4 mmol) of methanesulfonyl chloride was added dropwise, and the mixture was stirred for one hour.

After the completion of the reaction, a precipitate was separated from the reaction mixture by filtration to obtain a filtrate. The precipitate thus obtained in the form of a solid was washed with 10 ml of toluene, and the washings were added to the above obtained filtrate.

267 mg (2.2 mmol) of benzamide was dissolved in 10 ml of THF, and 247 mg (2.2 mmol) of potassium t-tuboxide was added thereto at room temperature. The thus obtained reaction mixture was then stirred for one hour. To this reaction mixture, the previously prepared reaction mixture of the washings and the filtrate was added dropwise at room temperature. With the addition of 68 mg (0.2 mmol) of tetra-n-butylammonium hydrogensulfate, the above reaction mixture was stirred for 30 minutes. The reaction mixture was then washed successively with water three times and brine, and dried. The solvent was distilled away from the reaction mixture, and a residue thus obtained was chromatographed on a silica gel column, so that (Z)-N-[4-[4-(piperidinomethyl)pyridyl-2-oxy]-2-butenyl]benzamide was obtained in a yield of 520 mg (71%).

$^1$H-NMR (δ, CDCl$_3$): 1.38–1.50 (2H, m), 1.50–1.72 (4H, m), 2.28–2.46 (4H, m), 3.43 (2H, s), 4.25 (2H, dd, J=6.6 Hz), 4.99 (2H, d, J=6 Hz), 5.76–5.94 (2H, m), 6.60 (1H, br-s), 6.79 (1H, s), 6.88 (1H, d, J=5 Hz), 7.39–7.50 (3H, m), 7.76–7.78 (2H, m), 7.98 (1H, d, J=5 Hz)

IR (ν, film): 3336, 2936, 1634, 1578, 1558, 1532, 1430, 1412, 1318, 1170, 1150, 1042, 988, 718 cm$^{-1}$

EXAMPLE 7

Synthesis of (Z)-N-[4-[4-(piperidinomethyl)pyridyl-2-oxy]-2-butenyl]trifluoroacetamide:

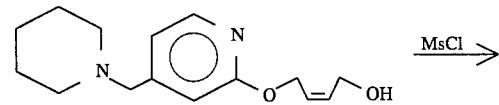

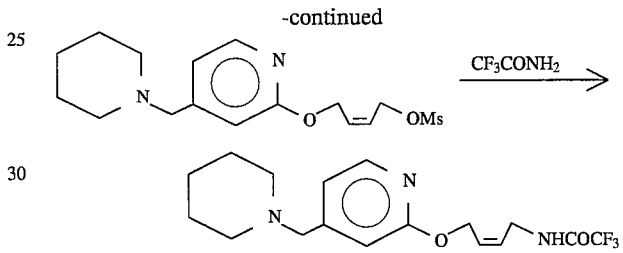

525 mg (2 mmol) of (Z)-N-4[4-(piperidinomethyl)pyridyl-2-oxy]-2-butenol and 253 mg (2.5 mmol) of triethylamine were dissolved in 10 ml of toluene. To this solution, 2 ml of a toluene solution containing 275 mg (2.4 mmol) of methanesulfonyl chloride was added dropwise at room temperature, and the mixture was stirred for one hour. After the completion of the reaction, a precipitate was separated from the reaction mixture by filtration to obtain a filtrate. The precipitate thus obtained in the form of a solid was washed with 10 ml of toluene, and the washings were added to the above obtained filtrate.

249 mg (2.2 mmol) of trifluoroacetamide was dissolved in 10 ml of THF. To the above solution, 247 mg (2.2 mmol) of potassium t-butoxide was added at room temperature, and the mixture was stirred for one hour. To this mixture, the previously prepared reaction mixture of the washings and the filtrate was added dropwise at room temperature. With the addition of 68 mg (0.2 mmol) of tetra-n-butylammonium hydrogensulfate,.the above obtained mixture was stirred for one hour. The reaction mixture was then washed successively with water three times and with brine, and dried. The solvent was distilled away from the reaction mixture, and a residue thus obtained was chromatographed on a silica gel column, so that (Z)-N-[4-[4-(piperidinomethyl)pyridyl-2-oxy]-2-butenyl]trifluoroacetamide was obtained in a yield of 410 mg (57%).

$^1$H-NMR (δ, CDCl$_3$): 1.38–1.52 (2H, m), 1.52–1.70 (4H, m), 2.26–2.54 (4H, m), 3.43 (2H, s), 4.16 (2H, dd, J=6.6 Hz), 4.95 (2H, d, J=7 Hz), 5.66–5.76 (1H, m), 5.85–5.95 (1H, m), 6.76 (1H, s), 6.92 (1H, d, J=5 Hz), 7.30–7.58 (1H, br-s), 8.02 (1H, d, J=5 Hz)

IR (ν, film): 2940, 1714, 1664, 1614, 1564, 1424, 1344, 1314, 1186, 1040, 998 cm$^{-1}$

EXAMPLE 8

Synthesis of (Z)-N-[4-[4-(piperidinomethyl)pyridyl-2-oxy]-2-butenyl]-2-(furfurylthio)acetamide:

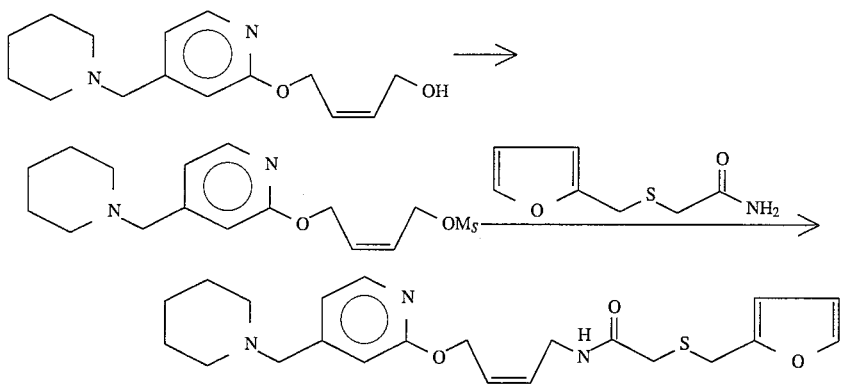

2.61 g (0.01 mol) of (Z)-N-4-[4-(piperidinomethyl)pyridyl-2-oxy]-2-butenol and 1.21 g (0.012 mol) of triethylamine were dissolved in 50 ml of toluene. To this solution, 10 ml of a toluene solution containing 1.26 g (0.011 mol) of methanesulfonyl chloride was added dropwise under an ice-cooled condition, and the mixture was stirred for one hour.

After the completion of the reaction, a precipitate was separated from the reaction mixture by filtration to obtain a filtrate. The precipitate thus obtained in the form of a solid was washed with 10 ml of toluene to obtain washings, and the washings were added to the above obtained filtrate.

1.71 g (0.01 mol) of 2-furfurylthioacetamide was dissolved in 20 ml of toluene. To this solution, 1.23 g (0.011 mol) of potassium t-butoxide was added at room temperature, and the mixture was stirred for one hour. To this mixture, the previously prepared reaction mixture of the washings and the filtrate was added dropwise at room temperature. The thus obtained reaction mixture was further stirred for 3 hours. The reaction mixture was then washed successively with water three times and brine, and dried. The solvent was distilled away from the reaction mixture, and the thus obtained residue was chromatographed on a silica gel column, so that (Z)-N-[4-[4-(piperidino-methyl)pyridyl-2-oxy]-2-butenyl]-2-(furfurylthio)acetamide was obtained in a yield of 3.74 g (90%).

$^1$H-NMR (δ, CDCl$_3$): 1.40–1.55 (2H, m), 1.55–1.80 (4H, m), 2.35–2.65 (4H, m), 3.23 (2H, s), 3.52 (2H, s), 3.75 (2H, s), 3.99 (2H, dd, J=6.6 Hz), 4.92 (2H, d, J=7 Hz), 5.56–5.68 (1H, m), 5.80–5.92 (1H, m), 6.20 (1H, d, J=3 Hz), 6.29 (1H, dd, J=3.2 Hz), 6.78 (1H, s), 6.88 (1H, br-s), 6.98 (1H, br-s), 7.35 (1H, d, J=2 Hz), 8.10 (1H, d, J=4 Hz)

IR (ν, film): 3300, 2940, 1655, 1620, 1560, 1420, 1405, 1300, 1150, 1040, 1010, 740 cm$^{-1}$ Furthermore, the above obtained (Z)-N-[4-[4-(piperidinomethyl)pyridyl-2-oxy]-2-butenyl]-2-(furfurylthio)acetamide was recrystallized in the form of an oxalate from ethanol, whereby the properties of the product were determined as follows:

Melting Point: 114°–115° C.

The results of the elemental analysis of the above compound were as follows:

|  | % C | % H | % N | % S |
|---|---|---|---|---|
| Calcd. | 57.02 | 6.18 | 8.31 | 6.34 |
| Found | 56.80 | 6.19 | 8.05 | 6.57 |

The above calculation was based on the formula for (Z)-N-[4-[4-(piperidinomethyl)pyridyl-2-oxy]-2-butenyl]-2-(furfurylthio)acetamide of C$_{24}$H$_{31}$N$_3$O$_7$S.

EXAMPLE 9

Synthesis of (Z)-N-[4-[4-(piperidinomethyl)pyridyl-2-oxy]-2-butenyl]-2-(furfurylsulfinyl)acetamide:

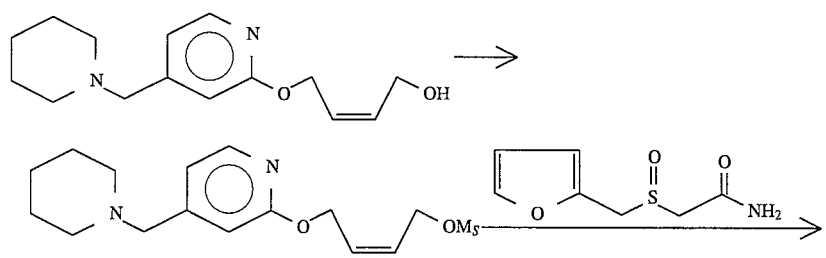

-continued

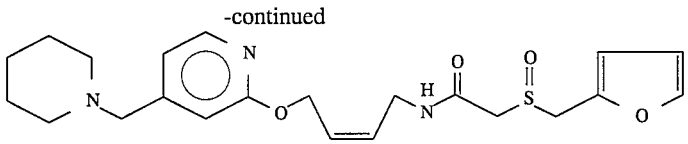

2.61 g (0.01 mol) of (Z)-N-4-[4-(piperidinomethyl)pyridyl-2-oxy]-2-butenol and 1.21 g (0.012 mol) of triethylamine were dissolved in 50 ml of toluene. To this solution, 10 ml of a toluene solution containing 1.26 g (0.011 mol) of methanesulfonyl chloride was added dropwise under an ice-cooled condition, and the mixture was stirred for one hour.

After the completion of the reaction, a precipitate was separated from the reaction mixture by filtration to obtain a filtrate. The precipitate thus obtained in the form of a solid was washed with 10 ml of toluene to obtain washings, and the washings were added to the above obtained filtrate.

1.87 g (0.01 mol) of 2-furfurylsulfinyl acetamide was dissolved in 20 ml of toluene. 1.23 g (0.011 mol) of potassium t-butoxide was added to the above solution at room temperature, and the mixture was stirred for one hour. To this mixture, the previously prepared reaction mixture of the washings and the filtrate was added dropwise at room temperature. The thus obtained mixture was stirred for three hours. The reaction mixture was then washed successively with water three times and brine, and dried. The solvent was distilled away from the reaction mixture, and a residue thus obtained was chromatographed on a silica gel column, so that (Z)-N-[4-[4-(piperidino-methyl)pyridyl-2-oxy]-2-butenyl]-2-(furfurylsulfinyl)acetamide was obtained in a yield of 3.24 g (75%).

Melting Point: 72.7°–73.4° C.

$^1$H-NMR (δ, CDCl$_3$): 1.40–1.50 (2H, m), 1.50–1.65 (4H, m), 2.30–2.45 (4H, m), 3.34 (1H, d, J=14 Hz), 3.40 (2H, s), 3.69 (1H, d, J=14 Hz), 4.14 (1H, d, J=14 Hz), 4.15 (2H, dd, J=6.6 Hz), 4.38 (1H, d, J=14 Hz), 4.93 (2H, dd, J=6.6 Hz), 5.60–5.75 (1H, m), 5.80–5.90 (1H, m), 6.40 (1H, dd, J=3.2 Hz), 6.47 (1H, d, J=5 Hz), 6.73 (1H, s), 7.20 (1H, br-s), 7.44 (1H, d, J=2 Hz), 8.04 (1H, d, J=5 Hz)

IR (ν, KBr): 3334, 2936, 1640, 1615, 1562, 1529, 1411, 1042 cm$^{-1}$

The results of the elemental analysis of the above compound were as follows:

|  | % C | % H | % N | % S |
|---|---|---|---|---|
| Calcd. | 61.23 | 6.77 | 9.74 | 7.43 |
| Found | 60.89 | 6.72 | 9.51 | 7.43 |

The above calculation was based on the formula for (Z)-N-[4-[4-(piperidinomethyl)pyridyl-2-oxy]-2-butenyl]-2-(furfurylsulfinyl)acetamide of C$_{22}$H$_{29}$N$_3$O$_4$S.

EXAMPLE 10

Synthesis of (Z)-N-acetyl-N-[4-[4-(piperidinomethyl)pyridyl-2-oxy]-2-butenyl]-2-(furfurylthio)acetamide:

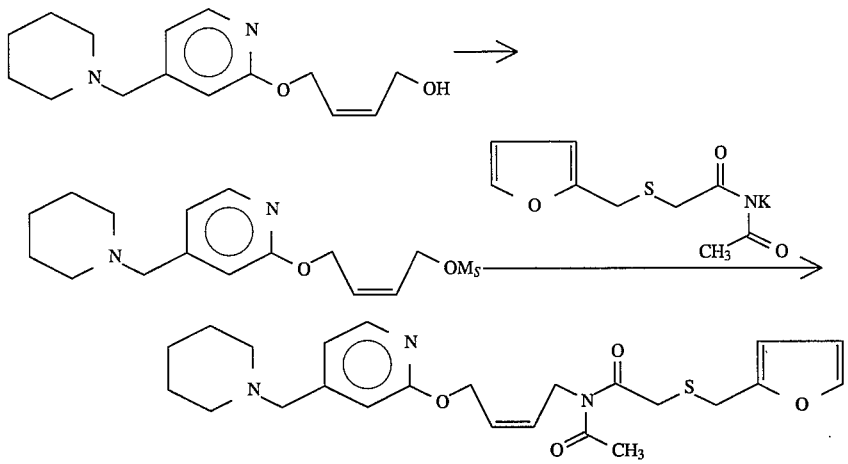

2.61 g (0.01 mol) of (Z)-N-4-[4-(piperidinomethyl)pyridyl-2-oxy]-2-butenol and 1.21 g (0.012 mol) of triethylamine were dissolved in 50 ml of toluene. To the above solution, 10 ml of a toluene solution containing 1.26 g (0.011 mol) of methanesulfonyl chloride was added dropwise at room temperature, and the mixture was stirred for one hour.

After the completion of the reaction, a precipitate was separated from the reaction mixture by filtration to obtain a filtrate. The precipitate thus obtained in the form of a solid was washed with 10 ml of toluene, and the washings were added to the above obtained filtrate.

2.13 g (0.01 mol) of N-acetyl-2-furfurylthioacetoamide was dissolved in 20 ml of toluene. To the above solution, 1.23 g (0.011 mol) of potassium t-butoxide was added at room temperature, and the mixture was stirred for one hour. To this mixture, the previously prepared reaction mixture of the washings and the filtrate was added dropwise at room temperature. The thus obtained reaction mixture was stirred for three hours. The mixture was then washed successively with water three times and brine, and dried. The solvent was distilled away, and the a residue thus obtained was chromatographed on a silica gel column for purification, so that (Z)-N-acetyl-N-[4-[4-(piperidinomethyl)pyridyl-2-oxy]-2-butenyl]-2-(furfurylthio)acetamide was obtained in a yield of 3.50 g (76%).

¹H-NMR (δ, CDCl₃): 1.35–1.55 (2H, m), 1.55–1.85 (4H, m), 2.41 (3H, s), 2.40–2.70 (4H, m), 3.12 (2H, br-s), 3.72 (2H, s), 3.80 (2H, s), 4.54 (2H, d, J=5 Hz), 4.94 (2H, d, J=5 Hz), 5.42–5.52 (1H, m), 5.82–5.92 (1H, m), 6.23 (1H, d, J=3 Hz), 6.30 (1H, dd, J=3.2 Hz), 6.81 (1H, s), 7.07 (1H, br-s), 7.35 (1H, d, J=2 Hz), 8.10 (1H, d, J=5 Hz)

IR (ν, neat): 2940, 1704, 1614, 1564, 1422, 1372, 1122

EXAMPLE 11

Synthesis of (Z)-N-[4-[4-(piperidinomethyl)pyridyl-2-oxy]-2-butenyl]-2-(furfurylthio)acetamide:

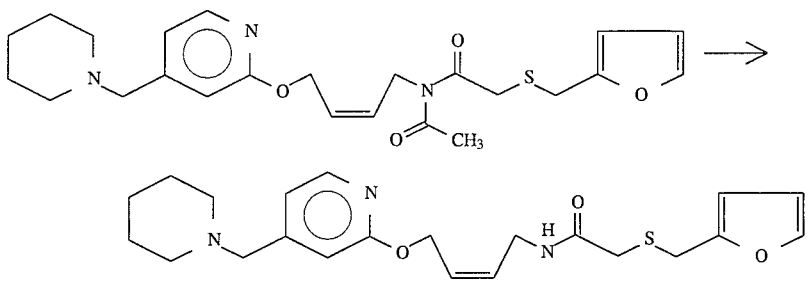

457 mg (1 mmol) of (Z)-N-acetyl-N-[4-[4-(piperidinomethyl)pyridyl-2-oxy]-2-butenyl]-2-(furfurylthio)acetoamide was dissolved in 10 ml of methanol. To this solution, 1 ml of 1N aqueous solution of sodium hydroxide was added under an ice-cooled condition, and the mixture was stirred for one hour.

After the completion of the reaction, the solvent was distilled away from the reaction mixture. A residue thus obtained was dissolved in ethyl acetate. The mixture was washed successively with water three times and brine. A resultant organic extract layer was dried, and the solvent was distilled away therefrom. A residue thus obtained was chromatographed on a silica gel column for purification, so that (Z)-N-[4-[4-(piperidinomethyl)pyridyl-2-oxy]-2-butenyl]-2-(furfurylthio)acetamide was obtained in a yield of 210 mg.

¹H-NMR (δ, CDCl₃): 1.40–1.55 (2H, m), 1.55–1.80 (4H, m), 2.35–2.65 (4H, m), 3.23 (2H, s), 3.53 (2H, s), 3.75 (2H, s), 3.99 (2H, dd, J=6.6 Hz), 4.92 (2H, d, J=7 Hz), 5.56–5.68 (1H, m), 5.80–5.92 (1H, m), 6.20 (1H, d, J=3 Hz), 6.29 (1H, dd, J=3.2 Hz), 6.78 (1H, s), 6.88 (1H, br-s), 6.98 (1H, br-s), 7.35 (H, d, J=2 Hz), 8.10 (1H, d, J=4 Hz)

EXAMPLE 12

Synthesis of (Z)-N-[4-[4-(piperidinomethyl)pyridyl-2-oxy]-2-butenyl]-2-(furfurylsulfinyl)acetamide:

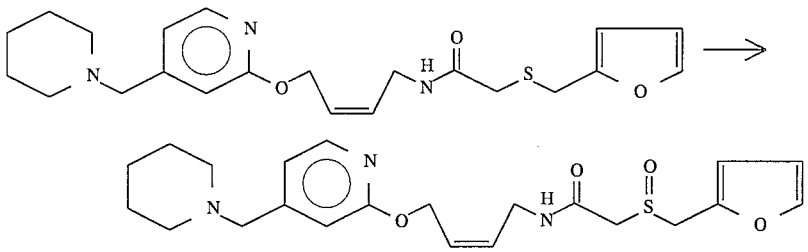

415 mg (1 mmol) of (Z)-N-[4-[4-(piperidinomethyl)pyridyl-2-oxy]-2-butenyl]-2-(furfurylthio)acetamide was dissolved in a mixture of 5 ml of methylene chloride and 5 ml of acetic acid. To this solution, 100 mg of a 30% aqueous solution of hydrogen peroxide was added under an ice-cooled condition, and the mixture was stirred for one hour.

After the completion of the reaction, with the addition of 10 ml of water, the reaction mixture was extracted with ethyl acetate. A resultant water layer was made basic by the addition of potassium carbonate, and extracted with ethyl acetate. A resultant organic extract layer was washed, successively with water three times and brine, and dried. The solvent was distilled away from the organic extract, and a residue thus obtained was chromatographed on a silica gel column for purification, so that (Z)-N-[4-[4-(piperidinomethyl)pyridyl-2-oxy]-2-butenyl]-2-(furfurylsulfinyl)acetamide was obtained in a yield of 360 mg (83%).

¹H-NMR (δ, CDCl₃): 1.40–1.50 (2H, m), 1.50–1.65 (4H, m), 2.30–2.45 (4H, m), 3.34 (1H, d, J=14 Hz), 3.40 (2H, s), 3.69 (1H, d, J=14 Hz), 4.14 (1H, d, J=14 Hz), 4.15 (2H, dd, J=6.6 Hz), 4.38 (1H, d, J=14 Hz), 4.93 (2H, dd, J=6.6 Hz), 5.60–5.75 (1H, m), 5.80–5.90 (1H, m), 6.40 (1H, dd, J=3.2 Hz), 6.47 (1H, d, J=5 Hz), 6.73 (1H, s), 7.20 (1H, br-s), 7.44 (1H, d, J=2 Hz), 8.04 (1H, d, J=5 Hz)

IR (ν, KBr): 3334, 2936, 1640, 1615, 1562, 1529, 1411, 1042

The results of the elemental analysis of the above compound were as follows:

|  | % C | % H | % N | % S |
|---|---|---|---|---|
| Calcd. | 61.23 | 6.77 | 9.74 | 7.43 |
| Found | 60.89 | 6.72 | 9.51 | 7.43 |

The above calculation was based on the formula for (Z)-N-[4-[4-(piridinomethyl)pyridyl-2-oxy]-2-butenyl]-2-(furfurylsulfinyl)acetamide of $C_{22}H_{29}N_3O_4S$.

EXAMPLE 13

Synthesis of (Z)-N-t-butoxycarbonyl-N-[4-[4-(piperidinomethyl)pyridyl-2-oxy]-2-butenyl]-2-(furfurylthio)acetamide:

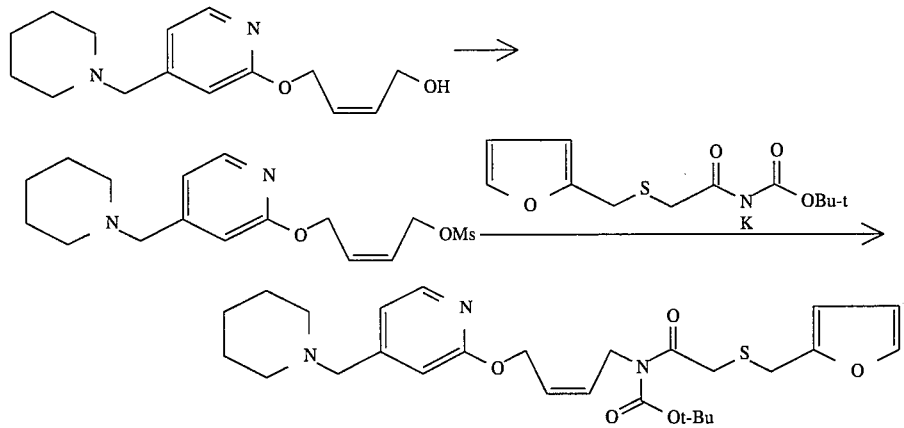

1.00 g (3.81 mmol) of (Z)-4-[4-(piperidinomethyl)pyridyl-2-oxy]-2-butenol and 0.66 ml (4.57 mmol) of triethylamine were dissolved in 30 ml of toluene. To this solution, 0.35 ml (4.57 mmol) of methanesulfonyl chloride was added dropwise under an ice-cooled condition, and the mixture was stirred for one hour. The thus obtained reaction mixture was washed with 1N aqueous solution of sodium hydroxide, and dried over anhydrous sodium sulfate to prepare a first reaction mixture.

1.14 g (4.19 mmol) of N-t-butoxycarbonyl-2-furfurylthioacetamide was dissolved in 20 ml of THF, followed by the addition of 1.14 g (4.19 mmol) of potassium t-butoxide under an ice-cooled condition. The thus obtained reaction mixture was then stirred at room temperature for 30 minutes, followed by the addition of 64 mg (0.19 mmol) of tetra-n-butylammonium hydrogensulfate thereto to obtain a second reaction mixture.

The previously prepared first reaction mixture was added dropwise to the above second reaction mixture at room temperature, and the mixture was stirred for four hours. The reaction mixture was washed successively with water and brine, and dried over anhydrous sodium sulfate. The solvent was distilled away from the reaction mixture, and a residue thus obtained was chromatographed on a silica gel column for purification, so that (Z)-N-t-butoxy-carbonyl-N-[4-[4-(piperidinomethyl)pyridyl-2-oxy]-2-butenyl]-2-(furfurylthio)acetamide was obtained in a yield of 1.69 g (86%).

$^1$H-NMR (δ, CDCl$_3$): 1.39–1.49 (2H, m), 1.50 (9H, s), 1.53–1.63 (4H, m), 2.30–2.42 (4H, m), 3.40 (2H, s), 3.77 (2H, s), 3.79 (2H, s), 4.45 (2H, d, J=16.3 Hz), 4.98 (2H, d, J=5.4 Hz), 5.52–5.63 (1H, m), 5.80–5.90 (1H, m), 6.24 (1H, d, J=3.3 Hz), 6.30 (1H, dd, J=5.0, 1.9 Hz), 6.71 (1H, s), 6.86 (1H, d, J=4.2 Hz), 7.36 (1H, d, J=2.0 Hz), 8.05 (1H, d, J=5.2 Hz)

IR (ν, neat): 2936, 1736, 1686, 1614 cm$^{-1}$

EXAMPLE 14

Synthesis of (Z)-N-[4-[4-(piperidinomethyl)pyridyl-2-oxy]-2-butenyl]-2-(fluorothio)acetamide:

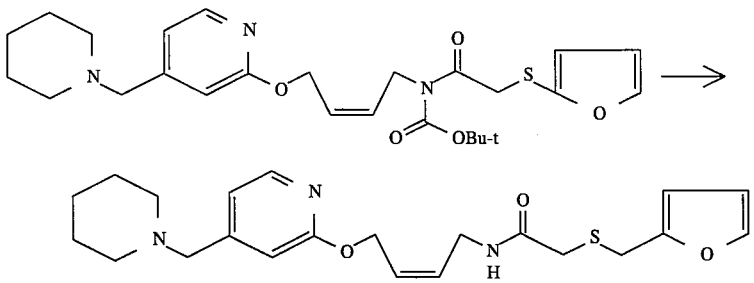

55 mg (0.11 mmol) of (Z)-N-t-butoxycarbonyl-N-[4-[4-(piperidinomethyl)pyridyl-2-oxy]-2-butenyl]-2-(fluorothio)acetamide was dissolved in 5 ml of methylene chloride. To this solution, 10.1 ml (1.30 mmol) of trifluoroacetic acid was added at room temperature, and the mixture was stirred for seven hours.

After the completion of the reaction, the thus obtained reaction mixture was neutralized with a 10% potassium carbonate, and extracted with ethyl acetate. A resultant organic extract layer was washed with brine, and dried over anhydrous sodium sulfate. The solvent was distilled away from the organic extract, and a residue thus obtained was chromatographed on a silica gel column for purification, so that (Z)-N-[4-[4-(piperidinomethyl)pyridyl-2-oxy]-2-butenyl]-2-(furfurylthio)acetamide was obtained in a yield of 36 mg (80%).

$^1$H-NMR (δ, CDCl$_3$): 1.40–1.55 (2H, m), 1.55–1.80 (4H, m), 2.35–2.65 (4H, m), 3.23 (2H, s), 3.53 (2H, s), 3.75 (2H, s), 3.99 (2H, dd, J=6.6 Hz), 4.92 (2H, d, J=7 Hz), 5.56–5.68 (1H, m), 5.80–5.92 (1H, m), 6.20 (1H, d, J=3 Hz), 6.29 (1H, dd, J=3.2 Hz), 6.78 (1H, s), 6.88 (1H, br-s), 6.98 (1H, br-s), 7.35 (1H, d, J=2 Hz), 8.10 (1H, d, J=4 Hz)

IR (v, film): 3300, 2940, 1655, 1620, 1560, 1420, 1405, 1300, 1150, 1040, 1010, 740 cm$^{-1}$ Furthermore, the above obtained (Z)-N-[4-[4-(piperidinomethyl)pyridyl-2-oxy]-2-butenyl]-2-(furfurylthio)acetamide was recrystallized in the form of an oxalate from ethanol, whereby the properties of the product were determined as follows:

Melting Point: 114°–115° C.

The results of the elemental analysis of the above compound were as follows:

|  | % C | % H | % N | % S |
|---|---|---|---|---|
| Calcd. | 57.02 | 6.18 | 8.31 | 6.34 |
| Found | 56.80 | 6.19 | 8.05 | 6.57 |

The above calculation was based on the formula for (Z)-N-[4-[4-(piperidinomethyl)pyridyl-2-oxy]-2-butenyl]-2-(furfurylthio)acetamide of $C_{24}H_{31}N_3O_7S$.

EXAMPLE 15

Synthesis of (Z)-N-formyl-N-[4-[4-(piperidinomethyl)pyridyl-2-oxy]-2-butenyl]-2-(furfurylthio)acetoamide:

over anhydrous sodium sulfate, whereby a first reaction mixture was obtained.

0.56 g (5.00 mmol) of potassium t-butoxide was suspended in 15 ml of THF, followed by the dropwise addition of 20 ml of a THF solution containing 1.0 g (5.00 mmol) of N-formyl-2-furfurylthioacetamide thereto under an ice-cooled condition. The thus obtained reaction mixture was stirred at room temperature for 30 minutes, followed by the addition of 84 mg (0.25 mmol) of tetra-n-butylammonium hydrogensulfate.

To this mixture, the previously obtained first reaction mixture was added dropwise at room temperature, and the mixture was stirred for five hours. The thus obtained reaction mixture was washed successively with water and brine, and dried over anhydrous sodium sulfate. The solvent was distilled away from the reaction mixture under reduced pressure, and a residue thus obtained was chromatographed on a silica gel column, so that (Z)-N-formyl-N-[4-[4-(piperidinomethyl)pyridyl-2-oxy]-2-butenyl]-2-(furfurylthio)acetamide was obtained in a yield of 1.6 g (79%).

Melting Point: 68.1°–70.3° C. (recrystallized from a mixed solvent of ethyl acetate and diethyl ether)

$^1$H-NMR (δ, CDCl$_3$): 1.35–1.50 (2H, m), 1.50–1.71 (4H, m), 2.25–2.60 (4H, m), 3.46 (2H, s), 3.53 (2H, s), 3.82 (2H, s), 4.49 (2H, d, J=6.9 Hz), 5.00 (2H, d, J=6.3 Hz), 5.43–5.55 (1H, m), 6.80–6.92 (1H, m), 6.27 (1H, d, J=2.9 Hz), 6.31

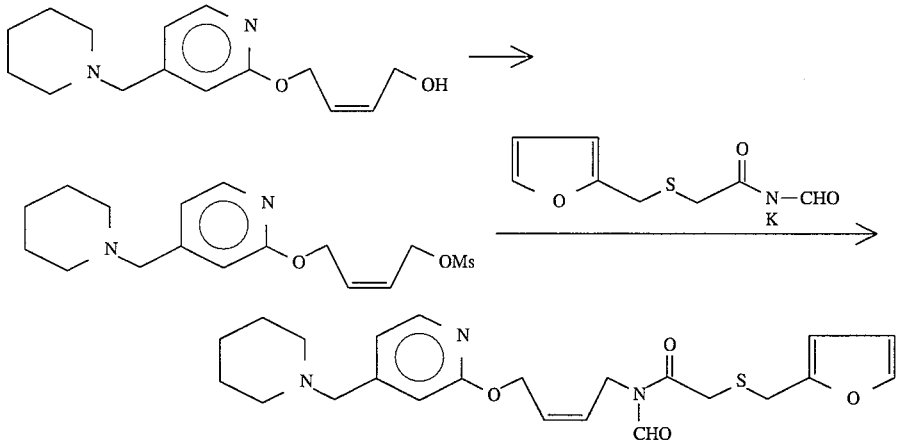

1.19 g (4.54 mmol) of (Z)-4-[4-(piperidinomethyl)pyridyl-2-oxy]-2-butenol and 0.79 ml (5.6 mmol) of triethylamine were dissolved in 35 ml of toluene. To this solution, 0.421 ml (5.44 mmol) of methanesulfonyl chloride was added dropwise under an ice-cooled condition, and the mixture was stirred at room temperature for 30 minutes. The thus obtained reaction mixture was washed successively with water and 1N solution of sodium hydroxide, and dried (1H, m), 6.74 (1H, s), 6.92 (1H, d, J=4.8 Hz), 7.37 (1H, d, J=2 Hz), 8.07 (1H, d, J=5.1 Hz), 9.19 (1H, s)

IR (v, KBr): 2928, 1660, 1614, 1556, 1308 cm$^{-1}$

EXAMPLE 16

Synthesis of (Z)-N-[4-[4-(piperidinomethyl)pyridyl-2-oxy]-2-butenyl]-2-(furfurylthio)acetamide:

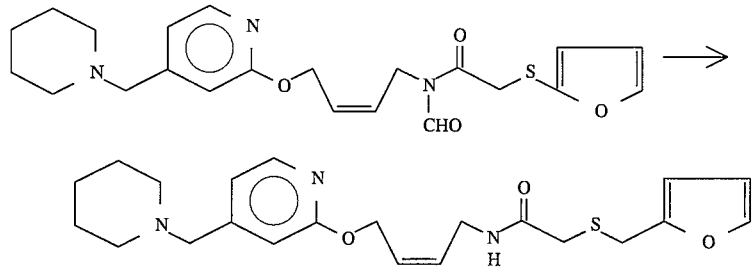

0.24 g (0.54 mmol) of (Z)-N-formyl-N-[4-[4-(piperidinomethyl)pyridyl-2-oxy]-2-butenyl]-2-(furfurylthio)acetamide was dissolved in 5 ml of methanol. To this solution, 0.226 g of p-toluene-sulfonic acid•monohydrate was added, and the mixture was stirred for 14 hours. With the addition of 30 ml of a aqueous solution of sodium hydrogencarbonate, the thus obtained reaction mixture was extracted with ethyl acetate twice. A resultant organic extract layer was washed with brine, and dried over anhydrous sodium sulfate. The solvent was distilled away from the organic extract under reduced pressure. A residue thus obtained was chromatographed on a silica gel column, so that (Z)-N-[4-[4-(piperidinomethyl)pyridyl-2-oxy]-2-butenyl]-2-(furfurylthio)acetamide was obtained in a yield of 157 mg (70%).

$^1$H-NMR (δ, CDCl$_3$): 1.40–1.55 (2H, m), 1.55–1.80 (4H, m), 2.35–2.65 (4H, m), 3.23 (2H, s), 3.53 (2H, s), 3.75 (2H, s), 3.99 (2H, dd, J=6.6 Hz), 4.92 (2H, d, J=7 Hz), 5.56–5.68 (1H, m), 5.80–5.92 (1H, m), 6.20 (1H, d, J=3 Hz), 6.29 (1H, dd, J=3.2 Hz), 6.78 (1H, s), 6.88 (1H, br-s), 6.98 (1H, br-s), 7.35 (1H, d, J=2 Hz), 8.10 (1H, d, J=4 Hz)

IR (ν, film): 3300, 2940, 1655, 1620, 1560, 1420, 1405, 1300, 1150, 1040, 1010, 740 cm$^{-1}$ Furthermore, the above obtained (Z)-N-[4-[4-(piperidinomethyl)pyridyl-2-oxy]-2-butenyl]-2-(furfurylthio)acetamide was recrystallized in the form of an oxalate from ethanol, whereby the properties of the product were determined as follows:

Melting Point: 114°–115° C.

The results of the elemental analysis of the above compound were as follows:

|  | % C | % H | % N | % S |
|---|---|---|---|---|
| Calcd. | 57.02 | 6.18 | 8.31 | 6.34 |
| Found | 56.80 | 6.19 | 8.05 | 6.57 |

The above calculation was based on the formula for (Z)-N-[4-[4-(piperidinomethyl)pyridyl-2-oxy]-2-butenyl]-2-(furfurylthio)acetamide of C$_{24}$H$_{31}$N$_3$O$_7$S.

EXAMPLE 17

Synthesis of (Z)-N-methoxycarbonyl-N-[4-[4-(piperidinomethyl)pyridyl-2-oxy]-2-butenyl]-2-(furfurylthio)acetamide:

(2.3 mmol) of methanesulfonyl chloride was added dropwise under an ice-cooled condition, and the mixture was stirred at room temperature for 30 minutes. The thus obtained reaction mixture was washed successively with water and 1N aqueous solution of sodium hydroxide, and dried over anhydrous sodium sulfate, whereby a first reaction mixture was obtained.

0.24 mg (2.1 mmol) of potassium t-butoxide was suspended in 5 ml of THF. To the above suspension, 15 ml of a THF solution containing 0.48 g (2.1 mmol) of N-methoxycarbonyl-2-furfurylthioacetamide was added dropwise under an ice-cooled condition. The thus obtained reaction mixture was stirred at room temperature for 30 minutes, and 0.048 g (0.095 mmol) of hexadecyl tributylphosphonium bromide was added thereto. The previously obtained first reaction mixture was added dropwise to the above obtained reaction mixture at room temperature, and the mixture was stirred for three hours. The thus obtained reaction mixture was washed successively with water and brine, dried over anhydrous sodium sulfate. The solvent was distilled away from the reaction mixture under reduced pressure, and a residue thus obtained was chromatographed on a silica gel column, so that (Z)-N-methoxycarbonyl-N-[4-[4-(piperidinomethyl)pyridyl-2-oxy]-2-butenyl]-2-(furfurylthio)acetamide was obtained in a yield of 0.86 g (95%).

$^1$H-NMR (δ, CDCl$_3$): 1.39–1.49 (2H, m), 1.53–1.67 (4H, m), 2.32–2.40 (4H, m), 3.41 (2H, s), 3.78 (2H, s), 3.80 (3H, s), 3.83 (2H, s), 4.50 (2H, d, J=7.2 Hz), 4.99 (2H, d, J=7.8 Hz), 5.51–5.63 (1H, m), 5.82–5.93 (1H, m), 6.24 (1H, d, J=2.7 Hz), 6.30 (1H, dd, J=2.0, 2.7 Hz), 6.73 (1H, s), 6.88 (1H, d, J=5.2 Hz), 7.36 (1H, d, J=2.0 Hz), 8.06 (1H, d, J=5.2 Hz)

IR (ν, neat): 2940, 1742, 1690, 1614, 1562 cm$^{-1}$

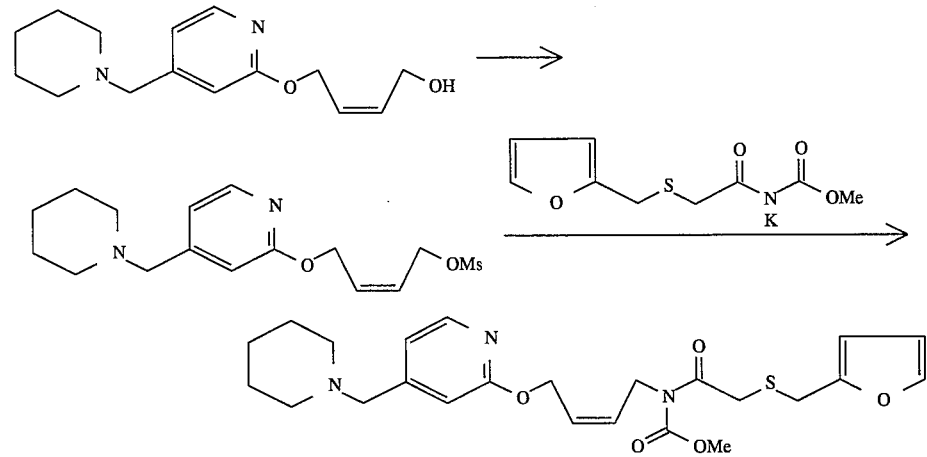

0.5 g (1.9 mmol) of (Z)-4-[4-(piperidinomethyl)pyridyl-2-oxy]-2-butenol and 0.33 ml (2.3 mmol) of triethylamine were dissolved in 30 ml of toluene. To this solution, 0.18 ml

EXAMPLE 18

Synthesis of (Z)-N-[4-[4-(piperidinomethyl)pyridyl-2-oxy]-2-butenyl]-2-(furfurylthio)acetamide:

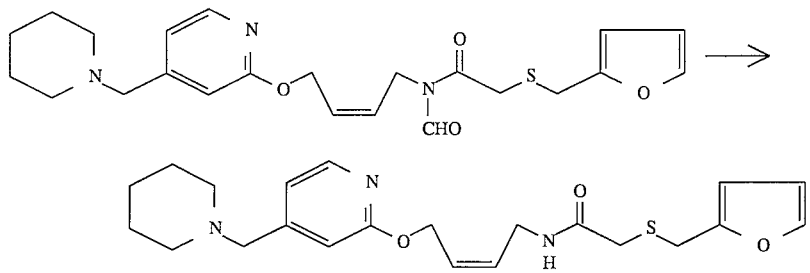

0.5 g (1.1 mmol) of (Z)-N-formyl-N-[4-[4-(piperidinomethyl)pyridyl-2-oxy]-2-butenyl]-2-(furfurylthio)acetamide was dissolved in 4 ml of tetrahydrofuran. To this solution, 2.3 ml of a tetrahydrofuran solution containing 2.3 mmol of isopropylamine was added dropwise under an ice-cooled condition, and the mixture was stirred at room temperature for 10 hours. After the completion of the reaction, the solvent was distilled away under reduced pressure from the reaction mixture. A residue thus obtained was dissolved in ethyl acetate, washed with brine, and dried over anhydrous sodium sulfate. The solvent was distilled away under reduced pressure, and a residue thus obtained was chromatographed on a silica gel column, so that (Z)-N-[4-[4-(piperidinomethyl)pyridyl-2-oxy]-2-butenyl]-2-(furfurylthio)acetamide was obtained in a yield of 0.41 g (86%).

$^1$H-NMR ($\delta$, CDCl$_3$): 1.40–1.55 (2H, m), 1.55–1.80 (4H, m), 2.35–2.65 (4H, m), 3.23 (2H, s), 3.52 (2H, s), 3.75 (2H, s), 3.99 (2H, dd, J=6.6 Hz), 4.92 (2H, d, J=7 Hz), 5.56–5.68 (1H, m), 5.80–5.92 (1H, m), 6.20 (1H, d, J=3 Hz), 6.29 (1H, dd, J=3.2 Hz), 6.78 (1H, s), 6.88 (1H, br-s), 6.98 (1H, br-s), 7.35 (1H, d, J=2 Hz), 8.10 (1H, d, J=4 Hz)

IR ($\nu$, film): 3300, 2940, 1655, 1620, 1560, 1420, 1405, 1300, 1150, 1040, 1010, 740 cm$^{-1}$ Furthermore, the above obtained (Z)-N-[4-[4-(piperidinomethyl)pyridyl-2-oxy]-2-butenyl]-2-(furfurylthio)acetamide was recrystallized in the form of an oxalate from ethanol, whereby the properties of the product were determined as follows:

Melting Point: 114°–115° C.

The results of the elemental analysis of the above compound were as follows:

|  | % C | % H | % N | % S |
|---|---|---|---|---|
| Calcd. | 57.02 | 6.18 | 8.31 | 6.34 |
| Found | 56.80 | 6.19 | 8.05 | 6.57 |

The above calculation was based on the formula for (Z)-N-[4-[4-(piperidinomethyl)pyridyl-2-oxy]-2-butenyl]-2-(furfurylthio)acetamide of C$_{24}$H$_{31}$N$_3$O$_7$S.

EXAMPLE 19

Synthesis of (Z)-N-[4-(tetrahydropyranyl-2-oxy)-2-butenyl]-2-(furfurylthio)acetamide:

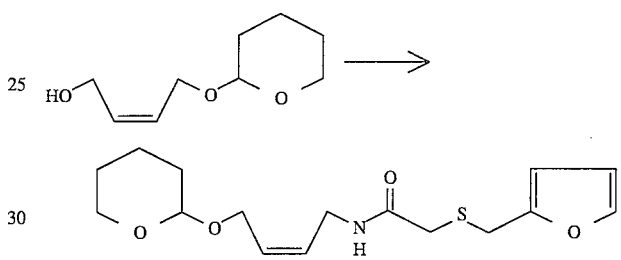

(1) 1.2 g of (Z)-4-(tetrahydropyranyl-2-oxy)-2-butene-1-ol and 0.76 g of triethylamine were dissolved in 30 ml of ethyl acetate. To this solution, 5 ml of an ethyl acetate solution containing 0.86 g of methanesulfonylchloride was added dropwise under an ice-cooled condition, and the mixture was stirred for one hour.

After the completion of the reaction, the reaction mixture was washed successively with water and brine. A resultant organic layer was dried, and the solvent was distilled away therefrom, whereby a reaction mixture was obtained.

(2) 0.79 g of 2-furfurylthioamide was dissolved in 10 ml of tetrahydrofuran. To this solution, 0.52 g of potassium t-butoxide was added at room temperature, and the mixture was stirred for 30 minutes. To this mixture, 10 ml of a tetrahydrofuran solution containing the reaction mixture obtained in the above (1) was added dropwise. The thus obtained mixture was stirred for three hours.

After the completion of the reaction, the solvent was distilled away under reduced pressure from the reaction mixture. A residue thus obtained was added to ethyl acetate, and washed successively with water and brine. A resultant organic layer was dried, and the solvent was distilled away therefrom. A residue thus obtained was chromatographed on a silica gel column, so that (Z)-N-[4-(tetrahydropyranyl-2-oxy)-2-butenyl]-2-(furfurylthio)acetamide was obtained in a yield of 1.1 g (78%).

$^1$H-NMR ($\delta$, CDCl$_3$): 1.40–1.90 (6H, m), 3.21 (2H, s), 3.50–3.60 (1H, m), 3.74 (2H, s), 3.70–3.95 (3H, m), 4.10 (1H, dd, J=10 Hz, 6 Hz), 4.30 (1H, dd, J=10 Hz, 6 Hz), 6.65 (1H, t, J=3 Hz), 5.52–5.63 (1H, m), 5.70–5.82 (1H, m), 6.21 (1H, d, J=3 Hz)

EXAMPLE 20

Synthesis of (Z)-N-(4-hydroxy-2-butenyl)-2-(furfurylthio)acetamide:

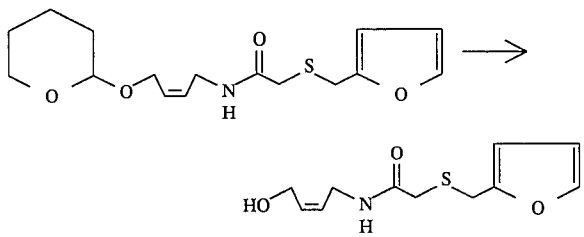

4.48 g of (Z)-N-[4-(tetrahydropyranyl-2-oxy)-2-butenyl]-2-(furfurylthio)acetamide was dissolved in 50 ml of methanol. To this solution, 2.75 g of p-toluene sulfonate was added, and the mixture was stirred for three hours.

After the completion of the reaction, the solvent was distilled away under reduced pressure from the reaction mixture. A residue thus obtained was added to ethyl acetate, and washed successively with water and brine. A resultant organic layer was dried, and the solvent was distilled away therefrom. A residue thus obtained was chromatographed on a silica gel column, so that (Z)-N-(4-hydroxy-2-butenyl)-2-(furfurylthio)acetoamide was obtained in a yield of 3.3 g (95%).

$^1$H-NMR (δ, CDCl$_3$): 3.21 (2H, s), 3.74 (2H, s), 3.88 (2H, t, J=6 Hz), 4.22 (2H, t, J=6 Hz), 5.38–5.52 (1H, m), 5.78–5.90 (1H, m), 6.21 (1H, d, J=3 Hz), 6.29–6.33 (1H, m), 6.95 (1H, br-s), 7.37 (1H, d, J=2 Hz)

EXAMPLE 21

Synthesis of (Z)-N-[4-[4-(piperidinomethyl)pyridyl-2-oxy]-2-butenyl]-N-2,4-dimethoxybenzyl-2-(furfurylthio)acetamide:

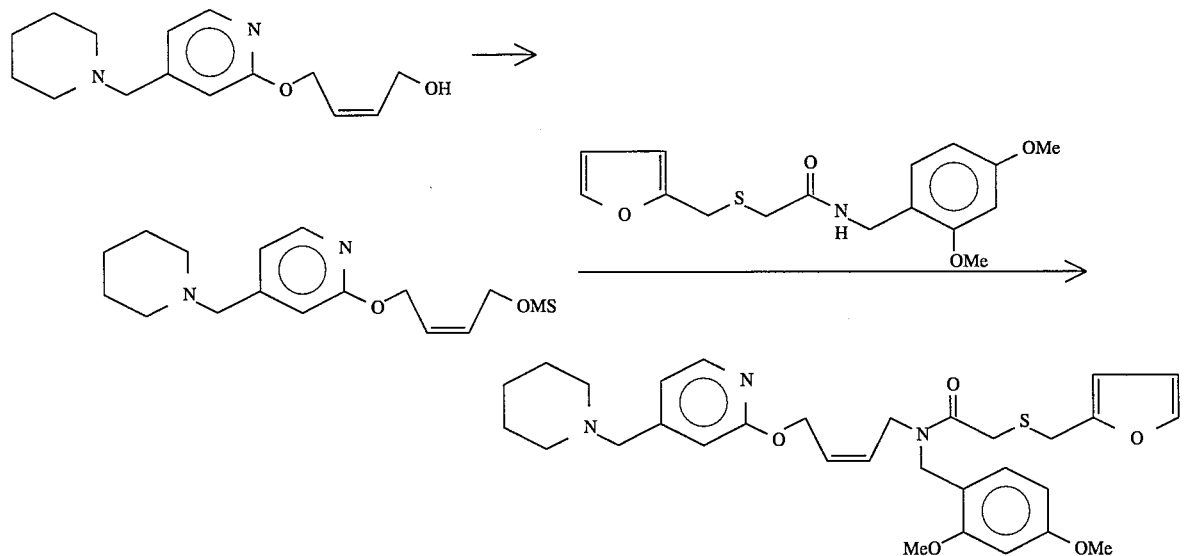

(1) 2.61 g (0.01 mol) of (Z)-N-4-[4-(piperidinomethyl)-pyridyl-2-oxy]-2-butenol and 1.21 g (0.012 mol) of triethylamine were dissolved in 50 ml of toluene. To this solution, 10 ml of a toluene solution containing 1.26 g (0.011 mol) of methanesulfonylchloride was added dropwise under an ice-cooled condition, and the mixture was stirred for one hour.

After the completion of the reaction, a precipitate was separated from the reaction mixture by filtration to obtain a filtrate. The precipitate thus obtained in the form of a solid was washed with 10 ml of toluene to obtain washings, and the washings were added to the above obtained filtrate to obtain a reaction mixture.

(2) 2.89 g (0.01 mol) of N-2,4-dimethoxybenzyl-2-furfurylthioacetamide was dissolved in 20 ml of toluene. To the above solution, 1.23 g (0.011 mol) of potassium t-butoxide was added at room temperature, and the mixture was stirred for one hour. To this mixture, the reaction mixture of the washings and the filtrate obtained in the above (1) was added dropwise at room temperature. The thus obtained reaction mixture was stirred for three hours, washed successively with water three times and brine, and dried. The solvent was distilled away from the reaction mixture, and a residue thus obtained was chromatographed on a silica gel column, so that (Z)-N-[4-[4-(piperidinomethyl)pyridyl-2-oxy]-2-butenyl]-N-2,4-dimethoxybenzyl-2-(furfurylthio)acetamide was obtained in a yield of 5.1 g (90%).

$^1$H-NMR (δ, CDCl$_3$): 1.40–1.65 (6H, m), 2.35 (4H, t, J=6 Hz), 3.37 (4H, s), 3.75 (3H, s), 3.76 (3H, s), 3.88 (2H, s), 4.05–4.20 (2H, m), 4.43 (1H, s), 4.57 (1H, s), 4.75–4.85 (2H, m), 5.75–5.80 (1H, m), 6.22–6.32 (2H, m), 6.35–6.45 (3H, m), 6.66 (1H, s), 6.82 (1H, d, J=3 Hz), 7.31 (1H, s), 7.97 (1H, d, J=3 Hz)

What is claimed is:

1. A method of producing an aminobutene derivative of formula (I), which comprises:

reacting a butene derivative of formula (II) with an amide derivative of formula (III):

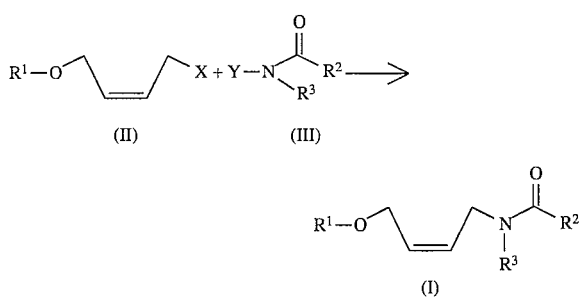

wherein R¹ represents hydrogen; a protective group for a hydroxyl group, an unsubstituted or substituted aromatic hydrocarbon group, or an unsubstituted or substituted heterocyclic group; X represents a hydroxyl group, a halogen atom, a sulfonyloxy group, an acyloxy group, an alkoxycarbonyloxy group, or a group which can form a cyclic sulfurous ester, sulfuric ester or carbonic acid ester in combination with R¹; Y represents an alkali metal, an alkaline earth metal, or hydrogen; R² represents hydrogen, an alkoxy group, an unsubstituted or substituted alkyl group selected from the group consisting of methyl, ethyl, propyl, butyl, chloromethyl, dichloromethyl, trichloromethyl, trifluoromethyl, benzyl, furfurylthiomethyl, furfurylsulfinylmethyl, and furfurylsulfonylmethyl, an unsubstituted or substituted aromatic hydrocarbon group, or an unsubstituted or substituted heterocyclic group, and R³ represents hydrogen, an unsubstituted or substituted acyl group, an alkoxy-carbonyl group, sulfonyl group or a substituted alkyl group.

2. The method of producing the aminobutene derivative as claimed in claim 1, wherein said protective group for hydroxyl group represented by R¹ in formula (II) is selected from the group consisting of tetrahydropyranyl group, methoxymethyl group, benzyloxymethyl group, ethoxyethyl group, 2-methoxyethyl group, t-butyl group, benzyl group, 4-methoxybenzyl group, diphenylmethyl group, triphenylmethyl group, trimethylsilyl group, triethylsilyl group, t-butyl dimethylsilyl group, formyl group, acetyl group, n-propionyl group, isopropionyl group, n-butyryl group, iso-butyryl group, valeryl group, iso-valeryl group, pivaloyl group, benzoyl group, naphthoyl group, methoxy-carbonyl group, ethoxycarbonyl group, iso-butoxycarbonyl group, allyloxycarbonyl group, benzyloxycarbonyl group, 9-fluorenylmethoxycarbonyl group, and phenyloxycarbonyl group.

3. The method of producing the aminobutene derivative as claimed in claim 1, wherein said aromatic hydrocarbon group represented by R¹ in formula (II) is selected from the group consisting of phenyl group, naphthyl group, anthranyl group, 3-(tetrahydropyranyl-2-oxymethyl)phenyl group, 3-(methoxymethoxymethyl)phenyl group, 3-formylphenyl group, 3-(diethoxymethyl)phenyl group, 3-(1,3-dioxolan-2-yl)phenyl group, 3-(piperidinomethyl)phenyl group, 3-(dimethylamino-methyl)phenyl group, 4-(tetrahydropyranyl-2-oxymethyl)-phenyl group, 4-(methoxymethoxymethyl)phenyl group, 4-formylphenyl group, 4-(diethoxymethyl)phenyl group, 4-(1,3-dioxolan-2-yl)phenyl group, 4-(piperidino-methyl)phenyl group, 4-(dimethylaminomethyl)phenyl group, 2-(tetrahydropyranyl-2-oxymethyl)phenyl group, 2-(methoxymethoxymethyl)phenyl group, 2-formylphenyl group, 2-(diethoxymethyl)phenyl group, 2-(1,3-dioxolan-2-yl)phenyl group, 2-(piperidinomethyl)phenyl group, and 2-(dimethyl aminomethyl)phenyl group.

4. The method of producing the aminobutene derivative as claimed in claim 1, wherein said heterocyclic group represented by R¹ in formula (II) is selected from the group consisting of pyridyl group, quinolyl group, isoquinolyl group, thienyl group, furyl group, 3-(tetrahydropyranyl-2-oxymethyl)-2-pyridyl group, 3-(methoxymethoxymethyl)-2-pyridyl group, 3-formyl-2-pyridyl group, 3-(diethoxymethyl)-2-pyridyl group, 3-(1,3-dioxolan-2-yl)-2-pyridyl group, 3-(piperidinomethyl)-2-pyridyl group, 3-(dimethylamino-methyl)-2-pyridyl group, 4-(tetrahydropyranyl-2-oxymethyl)-2-pyridyl group, 4-(methoxymethoxymethyl)-2-pyridyl group, 4-formyl-2-pyridyl group, 4-(diethoxymethyl)-2-pyridyl group, 4-(1,3-dioxolan-2-yl)-2-pyridyl group, 4-(piperidinomethyl)-2-pyridyl group, 4-(dimethylaminomethyl)-2-pyridyl group, 5-(tetrahydro-pyranyl-2-oxymethyl)-2-pyridyl group, 5-(methoxymethoxy-methyl)-2-pyridyl group, 5-formyl-2-pyridyl group, 5-(diethoxymethyl)-2-pyridyl group, 5-(1,3-dioxolan-2-yl)-2-pyridyl group, 5-(piperidinomethyl)-2-pyridyl group, and 5-(dimethylaminomethyl)-2-pyridyl group.

5. The method of producing the aminobutene derivative as claimed in claim 1, wherein said sulfonyloxy group represented by X in formula (II) is selected from the group consisting of methanesulfonyloxy group, trifluoro-methanesulfonyloxy group, benzene-sulfonyloxy group, p-toluenesulfonyloxy group, and imidazosulfonyloxy group.

6. The method of producing the aminobutene derivative as claimed in claim 1, wherein said acyloxy group represented by X in formula (II) is selected from the group consisting of formyloxy group, acetyloxy group, n-propionyloxy group, iso-propionyloxy group, n-butyryloxy group, iso-butyryloxy group, valeryloxy group, isovaleryloxy group, pivaloyloxy group, benzoyloxy group, and naphthoyloxy group.

7. The method of producing the aminobutene derivative as claimed in claim 1, wherein said alkoxycarbonyloxy group represented by X in formula (II) is selected from the group consisting of methoxycarbonyloxy group, ethoxycarbonyloxy group, iso-butoxycarbonyloxy group, allyloxycarbonyloxy group, benzyloxycarbonyloxy group, 9-fluorenylmethoxycarbonyloxy group, and phenyoxycarbonyloxy group.

8. The method of producing the aminobutene derivative as claimed in claim 1, wherein said alkoxyl group represented by R² in formula (III) is selected from the group consisting of methoxy group, ethoxy group, propoxy group, iso-butoxy group, t-butoxy group, and benzyloxy group.

9. The method of producing the aminobutene derivative as claimed in claim 1, wherein said aromatic hydrocarbon group represented by R² in formula (III) is selected from the group consisting of phenyl group, naphthyl group, and anthryl group, each unsubstituted or substituted with a substituent selected from the group consisting of an alkyl group, an alkoxyl group, a halogen atom, nitro group, and amino group.

10. The method of producing the aminobutene derivative as claimed in claim 1, wherein said heterocyclic group represented by R² in formula (III) is selected from the group consisting of pyridyl group, quinolyl group, isoquinolyl group, thienyl group, and furyl group, each unsubstituted or substituted with a substituent selected from the group consisting of an alkyl group, an alkoxyl group, a halogen atom, nitro group, and amino group.

11. The method of producing the aminobutene derivative as claimed in claim 1, wherein said acyl group represented by R³ in formula (III) is selected from the group consisting of formyl group, acetyl group, propionyl group, butyryl group, valeryl group, chloroacetyl group, dichloroacetyl group, trichloroacetyl group, trifluoroacetyl group, phenylacetyl group, benzoyl group, naphthoyl group, furoyl group, thenoyl group, nicotinoyl group, and isonicotinoyl group.

12. The method of producing the aminobutene derivative as claimed in claim 1, wherein said alkoxycarbonyl group represented by $R^3$ in formula (III) is selected from the group consisting of methoxycarbonyl group, ethoxycarbonyl group, iso-butoxycarbonyl group, allyloxycarbonyl group, benzyloxycarbonyl group, 9-fluorenylmethoxycarbonyl group, and phenyloxycarbonyl group.

13. The method of producing the aminobutene derivative as claimed in claim 1, wherein said sulfonyl group represented by $R^3$ in formula (III) is selected from the group consisting of methanesulfonyl group, trifluoromethanesulfonyl group, benzenesulfonyl group, p-toluenesulfonyl group, and imidazosulfonyl group.

14. The method of producing the aminobutene derivative as claimed in claim 1, wherein said substituted alkyl group represented by $R^3$ in formula (III) is selected from the group consisting of benzyl group, 4-methoxybenzyl group, and 2,4-dimethoxybenzyl group.

15. The method of producing the aminobutene derivative as claimed in claim 1, wherein $R^3$ in formula (III) is hydrogen, whereby an aminobutene derivative of formula (I-1) is produced:

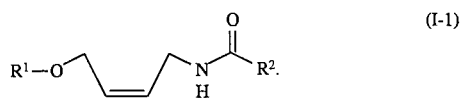

(I-1)

16. The method of producing the aminobutene derivative as claimed in claim 1, wherein $R^1$ is

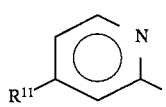

wherein $R^{11}$ represents hydroxymethyl group, tetrahydropyranyl-2-oxymethyl group, methoxymethoxymethyl group, formyl group, dimethoxymethyl group, diethoxymethyl group, 1,3-dioxolan-2-yl group, piperidinomethyl group, or dimethylamino methyl group;

X represents hydroxyl group, a halogen atom, methanesulfonyloxy group, trifluoromethanesulfonyloxy group, benzenesulfonyloxy group, p-toluene sulfonyloxy group, or imidazosulfonyloxy group;

$R^2$ represents

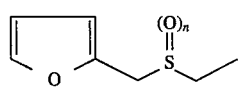

in which n is an integer of 0, 1 or 2; and $R^3$ represents hydrogen, whereby a pyridyloxy derivative of formula (I-3) is produced:

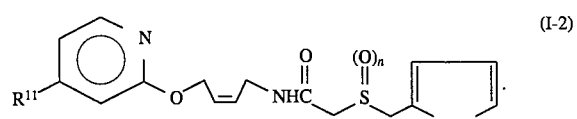

(I-2)

17. The method of producing the aminobutene derivative as claimed in claim 1, wherein $R^1$ is

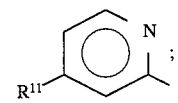

$R^2$ is

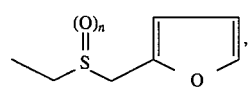

in which n is an integer of 0, 1, or 2; and $R^3$ is

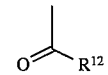

wherein $R^{11}$ represents hydroxymethyl group, tetrahydropyranyl-2-oxymethyl group, methoxymethoxymethyl group, formyl group, dimethoxymethyl group, diethoxymethyl group, 1,3-dioxolan-2-yl group, piperidinomethyl group, or dimethylaminomethyl group; $R^{12}$ represents hydrogen, an alkyl group having 1 to 6 carbon atoms, an unsubstituted or substituted aromatic hydrocarbon group, an alkoxyl group having 1 to 6 carbon atoms, or an unsubstituted or substituted aryloxy group, whereby an acetimide compound of formula (I-4) is produced:

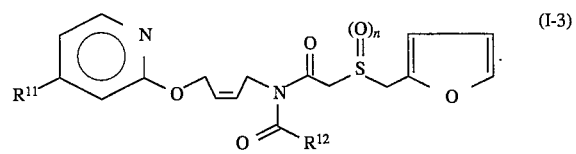

(I-3)

18. A method of producing an aminobutene derivative of formula (I-1) by subjecting an aminobutene derivative of formula (Ia) to deprotection:

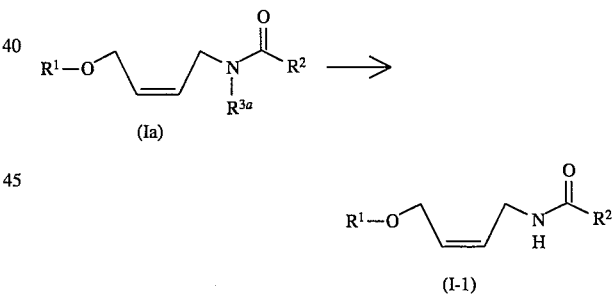

wherein $R^1$ represents hydrogen; a protective group for hydroxyl group, an unsubstituted or substituted aromatic hydrocarbon group, or an unsubstituted or substituted heterocyclic group; $R^2$ represents hydrogen, an alkoxyl group, an unsubstituted or substituted alkyl group, an unsubstituted or substituted aromatic hydrocarbon group, or an unsubstituted or substituted heterocyclic group; and $R^{3a}$ represents an unsubstituted or substituted acyl group, an alkoxy-carbonyl group, sulfonyl group, or a substituted alkyl group.

19. The method of producing the aminobutene derivative as claimed in claim 18, wherein $R^1$ is

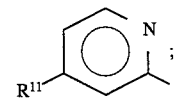

R² is

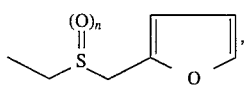

in which n is an integer of 0, 1, or 2; and R³ᵃ is

wherein R¹¹ represents hydroxymethyl group, tetrahydropyranyl-2-oxymethyl group, methoxymethoxymethyl group, formyl group, dimethoxymethyl group, diethoxymethyl group, 1,3-dioxolan-2-yl group, piperidinomethyl group, or dimethylaminomethyl group; R¹² represents hydrogen, an alkyl group having 1 to 6 carbon atoms, an unsubstituted or substituted aromatic hydrocarbon group, an alkoxyl group having 1 to 6 carbon atoms, or an unsubstituted or substituted aryloxy group, whereby a pyridyloxy derivative of formula (I-3) is produced:

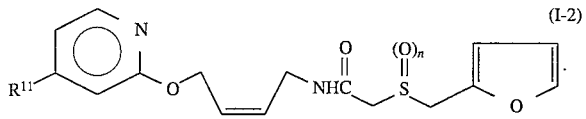

20. The method of producing the aminobutene derivative as claimed in claim 19, further comprising a step of oxidizing said pyridyloxy derivative of formula (I-3), whereby a pyridyloxy derivative of formula (I-4) is produced:

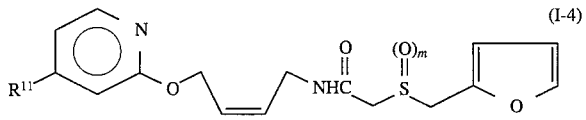

wherein R¹¹ is the same as in the formula (I-3), and m is n+1, in which n is 0 or 1.

21. A method of producing an aminobutene derivative of formula (I-4) by subjecting an aminobutene derivative of formula (I) to deprotection:

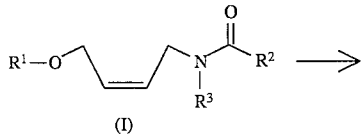

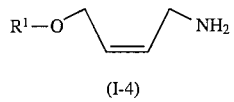

wherein R¹ represents hydrogen; a protective group for hydroxyl group, an unsubstituted or substituted aromatic hydrocarbon group, or an unsubstituted or substituted heterocyclic group; R² represents hydrogen, an alkoxy group, an unsubstituted or substituted alkyl group selected from the group consisting of methyl, ethyl, propyl, butyl, chloromethyl, dichloromethyl, trichloromethyl, trifluoromethyl, benzyl, furfurylthiomethyl, furfurylsulfinylmethyl, and furfurylsulfonylmethyl, an unsubstituted or substituted aromatic hydrocarbon group or an unsubstituted or substituted heterocyclic group; and R³ represents hydrogen, an unsubstituted or substituted acyl group, an alkoxy-carbonyl group, sulfonyl group, or a substituted alkyl group.

22. A method of producing an aminobutene derivative of formula (I-4) by subjecting an aminobutene derivative of formula (I-1) to deprotection:

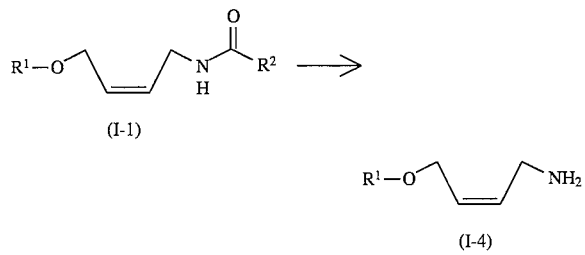

wherein R¹ represents hydrogen; a protective group for hydroxyl group, an unsubstituted or substituted aromatic hydrocarbon group, or an unsubstituted or substituted heterocyclic group; and R² represents hydrogen, an alkoxyl group, an unsubstituted or substituted alkyl group selected from the group consisting of methyl, ethyl, propyl, butyl, chloromethyl, dichloromethyl, trichloromethyl, trifluoromethyl, benzyl, furfurylthiomethyl, furfurylsulfinylmethyl, and furfurylsulfonylmethyl, an unsubstituted or substituted aromatic hydrocarbon group or an unsubstituted or substituted heterocyclic group.

23. The method of producing the aminobutene derivative of formula (I-1) as claimed in claim 18, wherein at least one of R²CO—, or R³ᵃ in formula (Ia) is formyl group, and said deprotection is carried out in an aprotic solvent in the presence of a primary amine or a secondary amine.

24. The method of producing the aminobutene derivative of formula (I-2) as claimed in claim 21, wherein at least one of R²CO—, or R³ in formula (I) is formyl group, and said deprotection is carried out in an aprotic solvent in the presence of a primary amine or a secondary amine.

* * * * *

UNITED STATES PATENT AND TRADEMARK OFFICE
CERTIFICATE OF CORRECTION

PATENT NO. : 5,616,711
DATED : April 1, 1997
INVENTOR(S) : Hiroshi IKAWA, et al.

It is certified that error appears in the above-identified patent and that said Letters Patent is hereby corrected as shown below:

Column 8, line 37, "dixanthiepin" should read --dioxanthiepin--.

Column 10, line 3, "0,001" should read --0.001--.

Column 11, line 39, "of formula of formula" should read --of formula--.
line 41, "imide" should read --amide--.

Column 18, line 63, "can used" should read --can be used--.

Column 29, line 36, "t-tuboxide" should read --t-butoxide--.

Column 34, line 66, "and the a residue" should read --and the residue--.

Column 36, line 52, "piridinomethyl" should read --piperidinomethyl--.

Signed and Sealed this

Sixteenth Day of June, 1998

*Attest:*

BRUCE LEHMAN

*Attesting Officer*  *Commissioner of Patents and Trademarks*